United States Patent [19]
Markland et al.

[11] Patent Number: 6,010,880
[45] Date of Patent: Jan. 4, 2000

[54] INHIBITORS OF HUMAN PLASMIN DERIVED FROM THE KUNITZ DOMAINS

[75] Inventors: William Markland, Milford, Mass.; Robert Charles Ladner, Ijamsville, Md.

[73] Assignee: Dyax Corp., Cambridge, Mass.

[21] Appl. No.: 08/676,124

[22] PCT Filed: Jan. 11, 1995

[86] PCT No.: PCT/US95/00298

§ 371 Date: Jan. 7, 1997

§ 102(e) Date: Jan. 7, 1997

[87] PCT Pub. No.: WO95/18830

PCT Pub. Date: Jul. 13, 1995

Related U.S. Application Data

[63] Continuation-in-part of application No. 08/208,265, Mar. 10, 1994, abandoned, which is a continuation-in-part of application No. 08/179,658, Jan. 11, 1994, abandoned.

[51] Int. Cl.$^7$ .............................. C07K 1/00; C07H 21/04; C12P 21/06; C12N 1/20
[52] U.S. Cl. ..................... 435/69.2; 530/300; 530/324; 536/23.5; 435/69.1; 435/252.3; 435/320.1
[58] Field of Search .................................... 530/380, 300; 435/69.1, 69.2, 189; 514/2, 12; 536/23.1, 23.2, 23.5

[56] References Cited

U.S. PATENT DOCUMENTS

| | | | |
|---|---|---|---|
| 4,118,481 | 10/1978 | Schnabel et al. | 424/177 |
| 4,153,687 | 5/1979 | Schnabel et al. | 424/177 |
| 5,223,409 | 6/1993 | Ladner et al. | 435/69.7 |

FOREIGN PATENT DOCUMENTS

| | | |
|---|---|---|
| WO-A-93 14120 | 7/1993 | WIPO . |
| WO-A-93 14121 | 7/1993 | WIPO . |
| WO-A-93 14122 | 7/1993 | WIPO . |

OTHER PUBLICATIONS

Adelman et al., Blood, 68(6):1280–1284 (1986).
Anba et al., Biochimie, 70(6):727–733 (1988).
Auerswald et al., Bio. Chem. Hoppe–Seyler, 369(Suppl):27–35 (1988).
Baneyx & Georgiou, J. Bacteriol., 173(8):2696–2703 (1991).
Baneyx and Georgiou, J. Bacteriol., 172(1):491–494 (1990).
Browne et al., GeneBank, Accession No. M74220 (1991).
Broze et al., Biochemisty, 29(33):7539–7546 (1990).
Colman et al., Hemostasis and Thrombosis, Second Edition (Colman et al., eds; ISBN 0–397–50679–1) Chap. 1, pp. 3–17 (1987).
Dennis and Lazarus, J. Biological Chem., 269(35):22129–22136 (1994).
Dennis and Lazarus, J. Biological Chem., 269(35):22137–22144 (1994).
Eigenbrot et al., Protein Engineering, 3(7):591–598 (1990).
Ellis et al., Ann. NY Acad. Sci., 667:13–31 (1992).
Fidler and Ellis, Cell, 79:185–188 (1994).
Fraedfich et al., Thorac. Cardiovasc. Surg., 37(2):89–91 (1989).
Gardell, Toxicol. Pathol., 21(2):190–198 (1993).
Girard et al., J. Biol. Chem., 266(8):5036–5041 (1991).
Girard et al., Nature, 338:518–20 (1989).
Cregg et al., Bio/Technology, 11:905–910 (1993).
Hoover et al., Biochemistry, 32:10936–10943 (1993).
Hynes et al., Biochemistry, 29:10018–10022 (1990).
Kido et al., Biochem. & Biophys. Res. Comm., 167(2):716–721 (1990).
Kido et al., J. Biol. Chem., 263(34):18104–18107 (1988).
Kurjan and Herkowwitz, Cell, 30:933–943 (1982).
Laskowski and Kato, Ann. Rev. Biochem., 49:593–626 (1980).
Leatherbarrow and Salacinski, Biochemistry, 30(44):1071710721 (1991).
Lohmann and Marshall, Refract. Corneal. Surg. 9(4):300–302 (1993).
Lucas et al., J. Biological Chem., 258(7):4249–4256 (1983).
Mann and Lundblad, Hemostasis and Thrombosis, Second Edition (Colman et al., eds; ISBN 0–397–50679–1) Chap 10, pp. 148–161 (1987).
Miyajima et al., Gene, 37:155–161 (1985).
Neuhaus et al., Lancet, 2(8668)924–925 (1989).
Novotny et al, J. Biol. Chem., 264(31):18832–18837 (1989).
O'Reilly et al., Cell, 79:315–328 (1994).
Park and Tulinsky, Biochemistry, 25(14):3977–3982 (1986).
Putterman, Acta Chir. Scand., 155(6–7:)367 (1989).
Robbins, Hemostasis and Thrombosis, Second Edition (Colman et al., eds; ISBN 0–397–50679–1), Chap. 21, pp. 340–357 (1987).
Schechter and Berger, Biochem. Biophys. Res. Commun. 32(5):898–902 (1968).
Schechter and Berger, Biochem. Biophys. Res. Commun., 27(2):157–162 (1967).
Schnabel et al., Biol. Chem. Hoppe–Seyler, 367:1167–1176 (1986).
Sheridan et al., Dis. Colon Rectum, 32(6):505–508 (1989).
Sprecher et al., PNAS USA, 91:3353–3357 (1994).
Van Dijl et al., EMBO J., 11(8):2819–2828 (1992).
Varadi and Patthy, Biochemistry, 23(9):2108–2112 (1984).
Varadi and Patthy, Biochemistry, 22(10):2440–2446 (1983).
Vedvick et al., J. Ind. Microbiol., 7:197–201 (1991).
Wagner et al., Biochem Biophy. Res. Comm., 186:1138–1145 (1992).
Wun et al., J. Biol. Chem. 263(13):6001–6004 (1988).
Kido et al. Biochem Biophys. Res. comm. 167(2):716–721, Mar. 16, 1990.

*Primary Examiner*—Rebecca E. Prouty
*Assistant Examiner*—Tekchand Saidha
*Attorney, Agent, or Firm*—Leon R. Yankwich; Kenneth P. Zwicker

[57] ABSTRACT

This invention relates to novel mutants of the first Kunitz domain ($K_1$) of the human lipoprotein-associated coagulation inhibitor (LACI) which inhibit plasmin. The invention also relates to other modified Kunitz domains that inhibit plasmin and to other plasmin inhibitors.

16 Claims, No Drawings

INHIBITORS OF HUMAN PLASMIN DERIVED FROM THE KUNITZ DOMAINS

The present application is a 371 or U.S. National Stage application of PCT/US95/00298, filed Jan. 11, 1995, which is a continuation-in-part of U.S. application Ser. No. 08/208,265, filed Mar. 10, 1994, now abandoned, which in turn is a continuation-in-part of Ser. No. 08/179, 658, filed Jan. 11, 1994, now abandoned. The entirety of each of these applications is hereby incorporated by reference.

BACKGROUND OF THE INVENTION

1. Field of the Invention

This invention relates to novel mutants of the first Kunitz domain ($K_1$) of the human lipoprotein-associated coagulation inhibitor LACI, which inhibit plasmin. The invention also relates to other modified Kunitz domains that inhibit plasmin and to other plasmin inhibitors.

2. Description of the Background Art

The agent mainly responsible for fibrinolysis is plasmin, the activated form of plasminogen. Many substances can activate plasminogen, including activated Hageman factor, streptokinase, urokinase (uPA), tissue-type plasminogen activator (tPA), and plasma kallikrein (pKA). pKA is both an activator of the zymogen form of urokinase and a direct plasminogen activator.

Plasmin is undetectable in normal circulating blood, but plasminogen, the zymogen, is present at about 3 $\mu$M. An additional, unmeasured amount of plasminogen is bound to fibrin and other components of the extracellular matrix and cell surfaces. Normal blood contains the physiological inhibitor of plasmin, $\alpha_2$-plasmin inhibitor ($\alpha_2$-PI), at about 2 $\mu$M. Plasmin and $\alpha_2$-PI form a 1:1 complex. Matrix or cell bound-plasmin is relatively inaccessible to inhibition by $\alpha_2$-PI. Thus, activation of plasmin can exceed the neutralizing capacity of $\alpha_2$-PI causing a profibrinolytic state.

Plasmin, once formed:
  i. degrades fibrin clots, sometimes prematurely;
  ii. digests fibrinogen (the building material of clots) impairing hemostasis by causing formation of friable, easily lysed clots from the degradation products, and inhibition of platelet adhesion/aggregation by the fibrinogen degradation products;
  iii. interacts directly with platelets to cleave glycoproteins Ib and IIb/IIIa preventing adhesion to injured endothelium in areas of high shear blood flow and impairing the aggregation response needed for platelet plug formation (ADEL86);
  iv. proteolytically inactivates enzymes in the extrinsic coagulation pathway further promoting a prolytic state. Robbins (ROBB87) reviewed the plasminogen-plasmin system in detail. ROBB87 and references cited therein are hereby incorporated by reference.

Fibrinolysis and Fibrinogenolysis

Inappropriate fibrinolysis and fibrinogenolysis leading to excessive bleeding is a frequent complication of surgical procedures that require extracorporeal circulation, such as cardiopulmonary bypass, and is also encountered in thrombolytic therapy and organ transplantation, particularly liver. Other clinical conditions characterized by high incidence of bleeding diathesis include liver cirrhosis, amyloidosis, acute promyelocytic leukemia, and solid tumors. Restoration of hemostasis requires infusion of plasma and/or plasma products, which risks immunological reaction and exposure to pathogens, e.g. hepatitis virus and HIV.

Very high blood loss can resist resolution even with massive infusion. When judged life-threatening, the hemorrhage is treated with antifibrinolytics such as $\epsilon$-amino caproic acid (See HOOV93) (EACA), tranexamic acid, or aprotinin (NEUH89). Aprotinin is also known as Trasylol™ and as Bovine Pancreatic Trypsin Inhibitor (BPTI). Hereinafter, aprotinin will be referred to as "BPTI". EACA and tranexamic acid only prevent plasmin from binding fibrin by binding the kringles, thus leaving plasmin as a free protease in plasma. BPTI is a direct inhibitor of plasmin and is the most effective of these agents. Due to the potential for thrombotic complications, renal toxicity and, in the case of BPTI, immunogenicity, these agents are used with caution and usually reserved as a "last resort" (PUTT89). All three of the antifibrinolytic agents lack target specificity and affinity and interact with tissues and organs through uncharacterized metabolic pathways. The large doses required due to low affinity, side effects due to lack of specificity and potential for immune reaction and organ/tissue toxicity augment against use of these antifibrinolytics prophylactically to prevent bleeding or as a routine postoperative therapy to avoid or reduce transfusion therapy. Thus, there is a need for a safe antifibrinolytic. The essential attributes of such an agent are:
  i. Neutralization of relevant target fibrinolytic enzyme(s);
  ii. High affinity binding to target enzymes to minimize dose;
  iii. High specificity for target, to reduce side effects; and
  iv. High degree of similarity to human protein to minimize potential immunogenicity and organ/tissue toxicity.

All of the fibrinolytic enzymes that are candidate targets for inhibition by an efficacious antifibrinolytic are chymotrypsin-homologous serine proteases.

Excessive Bleeding

Excessive bleeding can result from deficient coagulation activity, elevated fibrinolytic activity, or a combination of the two conditions. In most bleeding diatheses one must controll the activity of plasmin. The clinically beneficial effect of BPTI in reducing blood loss is thought to result from its inhibition of plasmin ($K_D$~0.3 nM) or of plasma kallikrein ($K_D$~100 nM) or both enzymes.

GARD93 reviews currently-used thrombolytics, saying that, although thrombolytic agents (e.g. tPA) do open blood vessels, excessive bleeding is a serious safety issue. Although tPA and streptokinase have short plasma half lives, the plasmin they activate remains in the system for a long time and, as stated, the system is potentially deficient in plasmin inhibitors. Thus, excessive activation of plasminogen can lead to a dangerous inability to clot and injurious or fatal hemorrhage. A potent, highly specific plasmin inhibitor would be useful in such cases.

BPTI is a potent plasmin inhibitor; it has been found, however, that it is sufficiently antigenic that second uses require skin testing. Furthermore, the doses of BPTI required to control bleeding are quite high and the mechanism of action is not clear. Some say that BPTI acts on plasmin while others say that it acts by inhibiting plasma kallikrein. FRAE89 reports that doses of about 840 mg of BPTI to 80 open-heart surgery patients reduced blood loss by almost half and the mean amount transfused was decreased by 74%. Miles Inc. has recently introduced Trasylin in USA for reduction of bleeding in surgery (See Miles product brochure on Trasylol, which is hereby incorporated by reference.) LOHM93 suggests that plasmin inhibitors may be useful in controlling bleeding in surgery of the eye.

SHER89 reports that BPTI may be useful in limiting bleeding in colonic surgery.

A plasmin inhibitor that is approximately as potent as BPTI or more potent but that is almost identical to a human protein domain offers similar therapeutic potential but poses less potential for antigenicity.

Angiogenesis

Plasmin is the key enzyme in angiogenesis. OREI94 reports that a 38 kDa fragment of plasmin (lacking the catalytic domain) is a potent inhibitor of metastasis, indicating that inhibition of plasmin could be useful in blocking metastasis of tumors (FIDL94). See also ELLI92. ELLI92, OREI94 and FIDL94 and the references cited there are hereby incorporated by reference.

Plasmin

Plasmin is a serine protease derived from plasminogen. The catalytic domain of plasmin (or "CatDom") cuts peptide bonds, particularly after arginine residues and to a lesser extent after lysines and is highly homologous to trypsin, chymotrypsin, kallikrein, and many other serine proteases. Most of the specificity of plasmin derives from the kringles' binding of fibrin (LUCA83, VARA83, VARA84). On activation, the bond between $ARG_{561}$-$Val_{562}$ is cut, allowing the newly free amino terminus to form a salt bridge. The kringles remain, nevertheless, attached to the CatDom through two disulfides (COLM87, ROBB87).

BPTI has been reported to inhibit plasmin with $K_D$ of about 300 pM (SCHN86). AUER88 reports that BPTI($R_{15}$) has $K_i$ for plasmin of about 13 nM, suggesting that $R_{15}$ is substantially worse than $K_{15}$ for plasmin binding. SCHN86 reports that BPTI in which the residues $C_{14}$ and $C_{38}$ have been converted to Alanine has $K_i$ for plasmin of about 4.5 nM. KIDO88 reports that APP-I has $K_i$ for plasmin of about 75 pM ($7.5 \times 10^{-11}$M), the most potent inhibitor of human plasmin reported so far. DENN94a reports, however, that APP-I inhibits plasmin with $K_i$=225 nM ($2.25 \times 10^{-7}$M). Our second and third library were designed under the assumption that APP-I is a potent plasmin binder. The selection process did not select APP-I residues at most locations and the report of DENN94a explains why this happened.

With recombinant DNA techniques, it is possible to obtain a novel protein by expressing a mutated gene encoding a mutant of the native protein gene. Several strategies for picking mutations are known. In one strategy, some residues are kept constant, others are randomly mutated, and still others are mutated in a predetermined manner. This is called "variegation" and is defined in Ladner et al. U.S. Pat. No. 5,223,409, which is incorporated by reference.

DENN94a and DENN94b report selections of Kunitz domains based on APP-I for binding to the complex of Tissue Factor with Factor VII$_a$. They did not use LACI-K1 as parental and did not use plasmin as a target. The highest affinity binder they obtained had $K_D$ for their target of about 2 nM. Our first-round selectants have affinity in this range, but our second round selectants are about 25-fold better than this.

Proteins taken from a particular species are assumed to be less likely to cause an immune response when injected into individuals of that species. Murine antibodies are highly antigenic in humans. "Chimeric" antibodies having human constant domains and murine variable domains are decidedly less antigenic. So called "humanized" antibodies have human constant domains and variable domains in which the CDRs are taken from murine antibodies while the framework of the variable domains are of human origin. "Humanized" antibodies are much less antigenic than are "chimeric" antibodies. In a "humanized" antibody, fifty to sixty residues of the protein are of non-human origin. The proteins of this invention comprise, in most cases, only about sixty amino acids and usually there are ten or fewer differences between the engineered protein and the parental protein. Although humans do develop antibodies even to human proteins, such as human insulin, such antibodies tend to bind weakly and the often do not prevent the injected protein from displaying its intended biological function. Using a protein from the species to be treated does not guarantee that there will be no immune response. Nevertheless, picking a protein very close in sequence to a human protein greatly reduces the risk of strong immune response in humans.

Kunitz domains are highly stable and can be produced efficiently in yeast or other host organisms. At least ten human Kunitz domains have been reported. Although APP-I was thought at one time to be a potent plasmin inhibitor, there are, actually, no human Kunitz domains that inhibit plasmin as well as does BPTI. Thus, it is a goal of the present invention to provide sequences of Kunitz domain that are both potent inhibitors of plasmin and close in sequence to human Kunitz domains.

The use of site-specific mutagenesis, whether nonrandom or random, to obtain mutant binding proteins of improved activity is known in the art, but success is not assured.

SUMMARY OF THE INVENTION

This invention relates to mutants of BPTI-homologous Kunitz domains that potently inhibit human plasmin. In particular, this invention relates to mutants of one domain of human LACI which are likely to be non-immunogenic to humans, and which inhibit plasmin with $K_D$, preferably, of about 5 nM or less, more preferably of about 300 pM or less, and most preferably about 100 pM or less. The invention also relates to the therapeutic and diagnostic use of these novel proteins.

Plasmin-inhibiting proteins are useful for the prevention or treatment of clinical conditions caused or exacerbated by plasmin, including inappropriate fibrinolysis or fibrinogenolysis, excessive bleeding associated with thrombolytics, post-operative bleeding, and inappropriate androgenesis. Plasmin-binding mutants, whether or not inhibitory, are useful for assaying plasmin in samples, in vitro, for imaging areas of plasmin activity, in vivo, and for purification of plasmin.

Preferred mutants QS4 and NS4 were selected from a library that allowed about 50 million proteins having variability at positions 13, 16, 17, 18, 19, 31, 32, 34, and 39. These proteins have an amino-acid sequence nearly identical to a human protein but inhibit plasmin with $K_i$ of about 2 nM (i.e. about 6-fold less potent than BPTI, but 100-fold better than APP-I).

An especially preferred protein, SPI11, was selected from a library allowing variability at positions 10, 11, 13, 15, 16, 17, 18, 19, and 21 and has an affinity for plasmin which is less than 100 pM (i.e. about 3-fold superior to BPTI in binding), and yet is much more similar in sequence to LACI, a human protein, than to the BPTI, a bovine protein. Other LACI-K1 mutants selected from this library and thought to have very high affinity for plasmin include SPI15, SPI08, and SPI23. An additional library allowing variation at positions 10, 11, 13, 15, 16, 17, 18, 19, 21, 31, 32, 34, 35, and 39 has been screened and a consensus sequence (SPIcon1)

found. Variants shown to be better than QS4, and thus more preferred, include SPI51 and SPI47. Sequences that are likely to have very high affinity for plasmin yet retain an essentially human amino-acid sequence have been identified and include sequences SPI60, SPI59, SPI42, SPI55, SPI56, SPI52, SPI46, SPI49, SPI53, SPI41, and SPI57. The amino-acid sequence information that confers high affinity for the active site of plasmin can be transferred to other Kunitz domains, particularly to Kunitz domains of human origin; designs of several such proteins are disclosed.

The preferred plasmin inhitors of the present invention fullfill one or more of the following desiderata:

1) the $K_i$ for plasmin is at most 20 nM, preferably not more than about 5 nM, more preferably not more than about 300 pM, and most preferably, not more than about 100 pM, 2) the inhibitor comprises a Kunitz domain meeting the requirements shown in Table 14 with residues number by reference to BPTI, 3) at the Kunitz domain positions 12–21 and 32–39 one of the amino-acid types listed for that position in Table 15, and 4) the inhibitor is more similar in amino-acid sequence to a reference sequence selected from the group SPI11, SPI15, SPI08, SPI23, SPI51, SPI47, QS4, NS4, Human LACI-K2, Human LACI-K3, Human collagen α3 KuDom, Human TFPI-2 DOMAIN 1, Human TFPI-2 DOMAIN 2, Human TFPI-2 DOMAIN 3, HUMAN ITI-K1, Human ITI-K2, HUMAN PROTEASE NEXIN-II, Human APP-I, DPI-1.1.1, DPI-1. 1.2, DPI-1.1.3, DPI-1.2.1, DPI-1.3.1, DPI-2.1, DPI-3.1.1, DPI-3.2.1, DPI-3.3.1, DPI-4.1.1, DPI-4.2.1, DPI-4.2.2, DPI-4.2.3, DPI-4.2.4, DPI-4.2.5, DPI-5.1, DPI-5.2, DPI-6.1, DPI-6.2 than is the amino acid sequence of said Kunitz domain to the sequence of BPTI.

NOMENCLATURE

Herein, affinities are stated as $K_D$ ($K_D(A,B)=[A][B]/[A-B]$). A numerically smaller $K_D$ reflects higher affinity. For the purposes of this invention, a "plasmin inhibiting protein" is one that binds and inhibits plasmin with $K_i$ of about 20 nM or less. "Inhibition" refers to blocking the catalytic activity of plasmin and so is measurable in vitro in assays using chromogenic or fluorogenic substrates or in assays involving macromolecules.

Amino-acid residues are discussed in three ways: full name of the amino acid, standard three-letter code, and standard single-letter code. Table use only the one-letter code. The text uses full names and three-letter code where clarity requires.

| A = Ala | G = Gly | M = Met | S = Ser |
| C = Cys | H = His | N = Asn | T = Thr |
| D = Asp | I = Ile | P = Pro | V = Val |
| E = Glu | K = Lys | Q = Gln | W = Trp |
| F = Phe | L = Leu | R = Arg | Y = Tyr |

For the purpose of this invention, "substantially homologous" sequences are at least 51%, more preferably at least 80%, identical, over any specified regions. Herein, sequences that are identical are understood to be "substantially homologous". Sequences would still be "substantially homologous" if within one region of at least 20 amino acids they are sufficiently similar (51% or more) but outside the region of comparison they differed totally. An insertion of one amino acid in one sequence relative to the other counts as one mismatch. Most preferably, no more than six residues, other than at termini, are different. Preferably, the divergence in sequence, particularly in the specified regions, is in the form of "conservative modifications".

"Conservative modifications" are defined as (a) conservative substitutions of amino acids as defined in Table 9; and (b) single or multiple insertions or deletions of amino acids at termini, at domain boundaries, in loops, or in other segments of relatively high mobility.

Preferably, except at termini, no more than about six amino acids are inserted or deleted at any locus, and the modifications are outside regions known to contain important binding sites.

Kunitz Domains

Herein "Kunitz domain" and "KuDom" are used interchangeably to mean a homologue of BPTI (not of the Kunitz soya-bean trypsin inhibitor). A KuDom is a domain of a protein having at least 51 amino acids (and up to about 61 amino acids) containing at least two, and preferably three, disulfides. Herein, the residues of all Kunitz domains are numbered by reference to BPTI (i.e. residues 1–58). Thus the first cysteine residue is residue 5 and the last cysteine is 55. An amino-acid sequence shall, for the purposed of this invention, be deemed a Kunitz domain if it can be aligned, with three or fewer mismatches, to the sequence shown in Table 14. An insertion or deletion of one residue shall count as one mismatch. In Table 14, "x" matches any amino acid and "X" matches the types listed for that position. Disulfides bonds link at least two of: 5 to 55, 14 to 38, and 30 to 51. The number of disulfides may be reduced by one, but none of the standard cysteines shall be left unpaired. Thus, if one cysteine is changed, then a compensating cysteine is added in a suitable location or the matching cysteine is also replaced by a non-cysteine (the latter being generally preferred). For example, *Drosophila funebris* male accessory gland protease inhibitor has no cysteine at position 5, but has a cysteine at position −1 (just before position 1); presumably this forms a disulfide to $CYS_{55}$. If $Cys_{14}$ and $Cys_{38}$ are replaced, the requirement of $Gly_{12}$, (Gly or $Ser)_{37}$, and $Gly_{36}$ are dropped. From zero to many residues, including additional domains (including other KuDoms), can be attached to either end of a Kunitz domain.

DETAILED DESCRIPTION OF THE PREFERRED EMBODIMENTS

Protease inhibitors, such as Kunitz domains, function by binding into the active site of the protease so that a peptide bond (the "scissile bond") is: 1) not cleaved, 2) cleaved very slowly, or 3) cleaved to no effect because the structure of the inhibitor prevents release or separation of the cleaved segments. In Kunitz domains, disulfide bonds act to hold the protein together even if exposed peptide bonds are cleaved. From the residue on the amino side of the scissile bond, and moving away from the bond, residues are conventionally called P1, P2, P3, etc. Residues that follow the scissile bond are called P1', P2', P3', etc. (SCHE67, SCHE68). It is generally accepted that each serine protease has sites (comprising several residues) S1, S2, etc. that receive the side groups and main-chain atoms of residues P1, P2, etc. of the substrate or inhibitor and sites S1', S2', etc. that receive the side groups and main-chain atoms of P1', P2', etc. of the substrate or inhibitor. It is the interactions between the S sites and the P side groups and main chain atoms that give the protease specificity with respect to substrates and the inhibitors specificity with respect to proteases. Because the fragment having the new amino terminus leaves the protease first, many worker designing small molecule protease inhibitors have concentrated on compounds that bind sites S1, S2, S3, etc.

LASK80 reviews protein protease inhibitors. Some inhibitors have several reactive sites on one polypeptide chain, and these domains usually have different sequences, specificities, and even topologies. It is known that substituting amino acids in the $P_5$ to $P_5'$ region influences the specificity of an inhibitor. Previously, attention has been focused on the P1 residue and those very close to it because these can change the specificity from one enzyme class to another. LASK80 suggests that among KuDoms, inhibitors with P1=Lys or Arg inhibit trypsin, those with P1=Tyr, Phe, Trp, Leu and Met inhibit chymotrypsin, and those with P1=Ala or Ser are likely to inhibit elastase. Among the Kazal inhibitors, LASK80 continues, inhibitors with P1=Leu or Met are strong inhibitors of elastase, and in the Bowman-Kirk family elastase is inhibited with P1=Ala, but not with P1=Leu. Such limited changes do not provide inhibitors of truly high affinity (i.e. better than 1 to 10 nM).

Kunitz domains are defined above. The 3D structure (at high resolution) of BPTI (the archetypal Kunitz domain) is known. One of the X-ray structures is deposited in the Brookhaven Protein Data Bank as "6PTI"]. The 3D structure of some BPTI homologues (EIGE90, HYNE90) are known. At least seventy KuDom sequences are known. Known human homologues include three KuDoms of LACI (WUNT88, GIRA89, NOVO89), two KuDoms of Inter-α-Trypsin Inhibitor, APP-I (KIDO88), a KuDom from collagen, and three KuDoms of TFPI-2 (SPRE94).

LACI

Lipoprotein-associated coagulation inhibitor (LACI) is a human serum phosphoglycoprotein with a molecular weight of 39 kDa (amino-acid sequence in Table 1) containing three KuDoms. We refer hereinafter to the protein as LACI and to the Kunitz domains thereof as LACI-K1 (residues 50 to 107), LACI-K2 (residues 121 to 178), and LACI-K3 (213 to 270). The cDNA sequence of LACI is reported in WUNT88. GIRA89 reports mutational studies in which the P1 residues of each of the three KuDoms were altered. LACI-K1 inhibits Factor VIIa (F.VII$_a$) when F.VII$_a$ is complexed to tissue factor and LACI-K2 inhibits Factor $X_a$. It is not known whether LACI-K3 inhibits anything. Neither LACI nor any of the KuDoms of LACI is a potent plasmin inhibitor.

KuDoms of this invention are substantially homologous with LACI-K1, but differ in ways that confer strong plasmin inhibitory activity discussed below. Other KuDoms of this invention are homologous to other naturally-occurring KuDoms, particularly to other human KuDoms. For use in humans, the proteins of this invention are designed to be more similar in sequence to a human KuDom than to BPTI, to reduce the risk of causing an immune response.

First Library of LACI-K1 and Selectants for Binding to Plasmin

Applicants have screened a first library of LACI-K1 for mutants having high affinity for human plasmin and obtained the sequences shown in Table 2 and Table 3. These sequences may be summarized as shown in Table 16, where "preferred residues" are those appearing in at least one of the 32 variants identified as binding plasmin. The preferences at residues 13, 16, 17, 18 and 19 are strong, as shown in Table 17. Although the range of types allowed at 31 and 32 is limited, the selection indicates that an acidic group at 31 and a neutral group at 32 is preferred. At residue 17, Arg was preferred; Lys, another positively charged amino acid, was not in the library, and may be a suitable substitute for Arg. Many amino-acid types at positions 34 and 39 are consistent with high-affinity plasmin binding, but some types may hinder binding.

It should be appreciated that Applicants have not sequenced all the positive isolates of this or other libraries herein disclosed, and that some of the possible proteins may not have been present in detectable amounts.

Applicants have prepared one of the selected proteins, QS4, shown in Table 2. QS4 inhibits plasmin with a $K_i$ of about 2 nM. Although this level of inhibition is less than that of BPTI, QS4 is a preferred molecule for use in humans because it has less potential for immunogenicity. Other proteins shown in Table 2 and Table 3 are very likely to be potent inhibitors of plasmin and are likely to pose little threat of antigenicity.

Second Library that Varies Residues 10–21

Applicants have prepared a second library of LACI-K1 derivatives shown in Table 5 and allowing variation at residues 10, 11, 13, 15, 16, 17, 18, 19, and 21. This was screened for binding to plasmin and the proteins shown in Table 6 were obtained.

"Consensus" in Table 6 is $\underline{E}_{10}TGPC\underline{RARFER}\underline{W}_{21}$, where the seven underscored residues differ from LACI-K1. Only acidic amino acids (Glu: 17 or Asp: 15) were seen at position 10; Lys and Asn are not acceptable. As Glu and Asp appeared with almost equal frequency, they probably contribute equally to binding. Acidic residues were not seen at position 11. Thr was most common (11/32) with Ser appearing often (9/32); Gly appeared 8 times. At 13, Pro was strongly preferred (24/32) with Ala second at 5/32. At 15, Arg was strongly preferred (25/32), but a few (7/32) isolates have Lys. Note that BPTI($R_{15}$) is a worse plasmin inhibitor than is BPTI. At 16, Ala was preferred (22/32), but Gly did appeared fairly often (10/32). At 17, Arg was most common (15/32), with Lys coming second (9/32). At residues 17 and 18, APP-I has Met and Ile. At 18, we allowed Ile or Phe. Only four isolates have Ile at 18 and none of these have Met at 17. This was surprising in view of KIDO88, but quite understandable in view of DENN94a. This collection of isolates has a broad distribution at 19: (Glu:8, Pro:7, Asp:4, Ala:3, His:3, Gly:2, Gln:2, Asn: 1, Ser:1, and Arg: 1), but acidic side groups are strongly preferred over basic ones. At 21, the distribution was (Trp:16, Phe:14, Leu:2, Cys:0); BPTI has Tyr at 21.

The binding of clonally pure phage that display one or another of these proteins was compared to the binding of BPTI phage (Table 6). Applicants have determined the $K_i$ of protein SPI11 and found it to be about 88 pM which is substantially superior to BPTI.

Third Library that Varies 10–21 and 31–39

Applicants used a pool of phage of the second library (varied at residues 10, 11, 13, 15, 16, 17, 18, 19, and 21) that had been selected twice for plasmin binding as a source of DNA into which variegation was introduced at residues 31, 32, 34, 35, and 39 as shown in Table 7.

This library was screened for three rounds for binding to plasmin and the isolates shown in Table 8 were obtained. The distribution of amino-acid types is shown in Table 18 where "x" means the amino-acid type was not allowed and "*" indicates the wild-type for LACI-K1.

These sequences gave a consensus in the 10–21 and 31–40 region of E$_{10}$TGPCRAKFDRW$_{21}$ ... E$_{31}$AFVYGGC GG$_{40}$ (SPIcon1 in Table 4). The ten underscored amino acids differ from LACI-K1. At eight varied positions, a second type was quite common: Asp at 10, Ala at 11, Glu at 19, Phe at 21,Thr at 31, Pro or Ser at 32,Leu or Ile at 34, and Glu at 39. At position 17, the highly potent inhibitor SPI11 has R. Thus, the sequence D$_{10}$TGPCRARFDRF$_{21}$ ... E$_{31}$ AFIYGGCEG$_{40}$ (DPI-1.1.1 in Table 4) differs from LACI-K1 by only six residues, matches the selected sequences at the residues having strong consensus, and has preferred substitutions at positions 10, 17, 21, 34, and 39. DPI-1.1.1 is expected to have a very high affinity for plasmin and little potential for immunogenicity in humans.

Preliminary testing of proteins SPI11, BPTI, SPI23, SPI51, SPI47, QS4, SPI22, SPI54, and SPI43 for plasmin inhibitory activity placed them in the order given. SPI11 is significantly more potent than BPTI with K$_i$ of about 88 pM. SPI23 and SPI51 are very similar in activity and only slightly less potent than BPTI. SPI47 is less potent than SPI51 but better than QS4. SPI22 is weaker than QS4. SPI54 and SPI43 are not so potent as QS4, K$_i$ probably>4 nM.

A KuDom that is highly homologous at residues 5–55 to any one of the sequences SPI11, SPI15, SPI08, SPI23, SPI51, SPI47, QS4, and NS4, as shown in Table 4, is likely to be a potent inhibitor (K$_D$>5 nM) of plasmin and have a low potential for antigenicity in humans. More preferably, to have high affinity for plasmin, a KuDom would have a sequence that is identical at residues 10–21 and 31–39 and has five or fewer differences at residues 5–9, 22–30, and 40–55 as compared to any of the sequences SPI11, SPI15, SPI08, SPI23, SPI51, SPI47, QS4, and NS4.

Using the selected sequences and the binding data of selected and natural KuDoms, we can write a recipe for a high-affinity plasmin-inhibiting KuDom that can be applied to other human KuDom parentals. First, the KuDom must meet the requirements in Table 14. The substitutions shown in Table 15 are likely to confer high-affinity plasmin inhibitory activity on any KuDom. Thus a protein that contains a sequence that is a KuDom, as shown in Table 14, and that contains at each of the position 12–21 and 32–39 an amino-acid type shown in Table 15 for that position is likely to be a potent inhibitor of human plasmin. More preferably, the protein would have an amino-acid type shown in Table 15 for all of the positions listed in Table 15. To reduce the potential for immune response, one should use one or another human KuDom as parental protein to give the sequence outside the binding region.

It is likely that a protein that comprises an amino-acid sequence that is substantially homologous to SPI11 from residue 5 through residue 55 (as shown in Table 4) and is identical to SPI11 at positions 13–19, 31, 32, 34, and 39 will inhibit human plasmin with a K$_i$ of 5 nM or less. SPI11 differs from LACI-K1 at 7 positions. It is not clear that these substitutions are equally important in fostering plasmin binding and inhibition. There are seven molecules in which one of the substituted positions of SPI11 is changed to the residue found in LACI-K1 (i.e. "reverted"), 21 in which two of the residues are reverted, 35 in which three residues are reverted, 35 in which four are reverted, 21 in which five are reverted, and seven in which six are reverted. It is expected that those with more residues reverted will have less affinity for plasmin but also less potential for immunogenicity. A person skilled in the art can pick a protein of sufficient potency and low immunogenicity from this collection of 126. It is also possible that substitutions in SPI11 by amino acids that differ from LACI-K1 can reduce the immunogenicity without reducing the affinity for plasmin to a degree that makes the protein unsuitable for use as a drug.

Designed KuDom Plasmin Inhibitors

Hereinafter, "DPI" will mean a "Designed Plasmin Inhibitor" that are KuDoms that incorporate amino-acid sequence information from the SPI series of molecules, especially SPI11. Sequences of several DPIs and their parental proteins are given in Table 4.

Sequences DPI-1.1.1, DPI-1.1.2, DPI-1.1.3, DPI-1.1.4, DPI-1.1.5, and DPI-1.1.6 (in Table 4) differ from LACI-K1 by 6, 5, 5, 4, 3, and 2 amino acids respectively and represent a series in which affinity for plasmin may decrease slowly while similarity to a human sequence increases so as to reduce likelihood of immunogenicity. The selections from each of the libraries show that M18F is a key substitution and that either I17K or I17R is very important. Selections from the second and third library indicate that Arg is strongly preferred at 15, that an acid side group at 11 is disadvantageous to binding. The highly potent inhibitor SPI11 differs from the consensus by having R$_{17}$, as does BPTI. DPI-1.1.1 carries the mutations D11T, K15R, I17R, M18F, K19D, and E32A, and is likely to be highly potent as a plasmin inhibitor. DPI-1.1.2 carries D11T, K15R, I17R, M18F, and K19D, and is likely to be highly potent. DPI-1.1.3 carries the mutations D11A, K15R, I17R, M18F, and K19D relative to LACI-K1. DPI-1.1.3 differs from DPI-1.1.2 by having A$_{11}$ instead of T$_{11}$; both proteins are likely to be very potent plasmin inhibitors. DPI-1.1.4 carries the mutations I17R, M18F, K19D, and E32A and should be quite potent. As DPI-1.1.4 has fewer of the SPI11 mutations, it may be less potent, but is also less likely to be immunogenic. DPI-1.1.5 carries the mutations I17R, M18F, and K19D. This protein is likely to be a good inhibitor and is less likely to be immunogenic. DPI-1.1.6 carries only the mutations I17R and M18F but should inhibit plasmin.

Protein DPI-1.2.1 is based on human LACI-K2 and shown in Table 4. The mutations P11T, I13P, Y17R, I18F, T19D, R32E, K34I, and L39E are likely to confer high affinity for plasmin. Some of these substitutions may not be necessary; in particular, P11T and T19D may not be necessary. Other mutations that might improve the plasmin affinity include E9A, D10E, G16A, Y21W, Y21F, R32T, K34V, and L39G.

Protein DPI-1.3.1 (Table 4) is based on human LACI-K3. The mutations R11T, L13P, N17R, E18F, N19D, R31E, P32E, K34I, and S36G are intended to confer high affinity for plasmin. Some of these substitutions may not be necessary; in particular, N19D and P32E may not be necessary. Other changes that might improve K$_D$ include D10E, N17K, F21W and G39E.

Protein DPI-2.1 (Table 4) is a based on the human collagen α3 KuDom. The mutations E11, T13P, D16A, F17R, I18F, L19D, A31E, R32E, and W34I are likely to confer high affinity for plasmin. Some of these substitutions may not be necessary; in particular, L19D and A31E may not be necessary. Other mutations that might improve the plasmin affinity include K9A, D10E, D16G, K20R, R32T, W34V, and G39E.

DPI-3.1.1 (Table 4) is derived from Human TFPI-2 domain 1. The exchanges Y11T, L17R, L18F, L19D, and R31E are likely to confer high affinity for plasmin. The mutation L19D may not be needed. Other mutations that might foster plasmin binding include Y21W, Y21F, Q32E, L34I, L34V, and E39G.

DPI-3.2.1 (Table 4) is derived from Human TFPI-2 domain 2. This parental domain contains insertions after residue 9 (one residue) and 42 (two residues). The mutations ($V_9$SVDDQC$_{14}$ replaced by $V_9$ETGPC$_{14}$), E15R, S17K, T18F, K32T, F34V, and ($H_{39}$RNRIENR$_{44}$ replaced by ($E_{39}$GNRNR$_{44}$) are likely to confer affinity for plasmin. Because of the need to change the number of amino acids, DPI-3.2.1 has a higher potential for immunogenicity than do other modified human KuDoms.

DPI-3.3.1 (Table 4) is derived from human TFPI-2, domain 3. The substitutions E11T, L13P, S15R, N17R, V18F, T34I, and T36G are likely to confer high affinity for plasmin. The mutations E11T, L13P, and T34I may not be necessary. Other mutations that might foster plasmin binding include D10E, T19D, Y21W, and G39E.

DPI-4.1.1(Table 4) is from human ITI-K1 by assertion of S10E, M15R, M17K, T18F, Q34V, and M39G. The mutations M39G and Q34V may not be necessary. Other mutations that should foster plasmin binding include: A11T, G16A, M17R, S19D, Y21W, and Y21F.

DPI-4.2.1(Table 4) is from human ITI-K2 through the mutations V10D, R11T, F17R, I18F, and P34V. The mutation P34V might not be necessary. Other mutation that should foster plasmin binding include: V10E, Q19D, L20R, W21F, P34L, and Q39E. DPI-4.2.2 is an especially preferred protein as it has only three mutations: R11T, F17R, and I18F. DPI-4.2.3 is an especially preferred protein as it has only four mutations: R11T, F17R, I18F, and L20R. DPI-4.2.4 is an especially preferred protein as it has only five mutations: R11T, F17R, I18F, L20R, and P34V. DPI-4.2.5 carries the muations V10E, R11T, F17R, I18F, L20R, V31E, L32T, P34V, and Q39G and is highly likely to inhibit plasmin very potently. Each of the proteins DPI-4.2.1, DPI-4.2.2, DPI-4.2.3, DPI-4.2.4, and DPI-4.2.5 is very likely to be a highly potent inhibitor of plasmin.

Before DENN94a, it was thought that APP-I was a very potent plasmin inhibitor. Thus, it was surprising to select proteins from a library that was designed to allow the APP-I residues at positions 10–21 which differed strongly from APP-I. Nevertheless, APP-I can be converted into a potent plasmin inhibitor. DPI-5.1 is derived from human APP-I (also known as Protease Nexin-II) by mutations M17R and I18F and is likely to be a much better plasmin inhibitor than is APP-I itself DPI-5.2 carries the further mutations S19D, A31E, and F34I which may foster higher affinity for plasmin.

DPI-6.1 is derived from the HKI B9 KuDom (NORR93) by the five substitutions: K11T, Q15R, T16A, M17R, and M18F. DPI-6.1 is likely to be a potent plasmin inhibitor. DPI-6.2 carries the additional mutations T19D and A34V which should foster plasmin binding.

Although BPTI is the best naturally-occurring KuDom plasmin inhibitors known, it could be improved. DPI-7.1 is derived from BPTI by the mutation I18F which is likely to increase the affinity for plasmin. DPI-7.2 carries the further mutation K15R which should increase plasmin binding. DPI-7.3 carries the added mutation R39G. DPI-7.4 carries the mutations Y10D, K15R, I18F, I19D, Q31E, and R39G and should have a very high affinity for plasmin.

MODIFICATION OF KUNITZ DOMAINS

KuDoms are quite small; if this should cause a pharmacological problem, such as excessively quick elimination from circulation, two or more such domains may be joined. A preferred linker is a sequence of one or more amino acids. A preferred linker is one found between repeated domains of a human protein, especially the linkers found in human BPTI homologues, one of which has two domains (BALD85, ALBR83b) and another of which has three (WUNT88). Peptide linkers have the advantage that the entire protein may then be expressed by recombinant DNA techniques. It is also possible to use a nonpeptidyl linker, such as one of those commonly used to form immunogenic conjugates. An alternative means of increasing the serum residence of a BPTI-like KuDom is to link it to polyethyleneglycol, so called PEGylation (DAVI79).

WAYS TO IMPROVE SPECIFICITY OF SPI11 and other KuDom plasmin inhibitors

Because we have made a large part of the surface of the KuDom SPI11 complementary to the surface of plasmin, $R_{15}$ is not essential for specific binding to plasmin. Many of the enzymes in the clotting and fibrinolytic pathways cut preferentially after Arg or Lys. Not having a basic residue at the P1 position may give rise to greater specificity. The variant SPI11-R15A (shown in Table 11), having an ALA at P1, is likely to be a good plasmin inhibitor and may have higher specificity for plasmin relative to other proteases than does SPI11. The affinity of SPI11-R15A for plasmin is likely to be less than the affinity of SPI11 for plasmin, but the loss of affinity for other Arg/Lys-preferring enzymes is likely to be greater and, in many applications, specificity is more important than affinity. Other mutants that are likely to have good affinity and very high specificity include SPI11-R15G and SPI11-R15N-E32A. This approach could be applied to other high-affinity plasmin inhibitors.

INCREASING THE AFFINITY OF SPI11

Variation of SPI11 as shown in Table 12 and selection of binders is likely to produce a Kunitz domain having affinity for plasmin that is higher than SPI11. This fourth library allows variegation of the 14–38 disulfide. The two segments of DNA shown are synthesized and used with primers in a PCR reaction to produce ds DNA that runs from NsiI to BstEII. The primers are identical to the 5' ends of the synthetic bits shown and of length 21 for the first and 17 for the second. As the variability is very high, we would endeavor to obtain between $10^8$ and $10^9$ transformants (the more the better).

MODE OF PRODUCTION

Proteins of this invention may be produced by any conventional technique, including a) nonbiological synthesis by sequential coupling of components, e.g. amino acids, b) production by recombinant DNA techniques in suitable host cells, and c) semisynthesis, for example, by removal of undesired sequences from LACI-K1 and coupling of synthetic replacement sequences.

Proteins disclosed herein are preferably produced, recombinantly, in a suitable host, such as bacteria from the genera Bacillus, Escherichia, Salmonella, Erwinia, and yeasts from the genera Hansenula, Kluyveromyces, Pichia, Rhinosporidium, Saccharomyces, and Schizosaccharomyces, or cultured mammalian cells such as COS-1. The more preferred hosts are microorganisms of the species *Pichia pastois, Bacillus subtilis, Bacillus brevis, Saccharomyces cerevisiae, Escherichia coil* and *Yarrowia lipolytica*. Any promoter which is functional in the host cell may be used to control gene expression.

Preferably the proteins are secreted and, most preferably, are obtained from conditioned medium. Secretion is the preferred route because proteins are more likely to fold correctly and can be produced in conditioned medium with few contaminants. Secretion is not required.

Unless there is a specific reason to include glycogroups, we prefer proteins designed to lack N-linked glycosylation sites to reduce potential for antigenicity of glycogroups and so that equivalent proteins can be expressed in a wide variety of organisms including: 1) *E. coli*, 2) *B. subtilis*, 3) *P. pastoris*, 4) *S. cerevisiae*, and 5) mammalian cells.

Several means exist for reducing the problem of host cells producing proteases that degrade the recombinant product; see, inter alia BANE90 and BANE91. VAND92 reports that overexpression of the *B. subtilis* signal peptidase in *E. coli*. leads to increased expression of a heterologous fusion protein. ANBA88 reports that addition of PMSF (a serine proteases inhibitor) to the culture medium improved the yield of a fusion protein.

Other factors that may affect production of these and other proteins disclosed herein include: 1) codon usage (optimizing codons for the host is preferred), 2) signal sequence, 3) amino-acid sequence at intended processing sites, presence and localization of processing enzymes, deletion, mutation, or inhibition of various enzymes that might alter or degrade the engineered product and mutations that make the host more permissive in secretion (permissive secretion hosts are preferred).

Reference works on the general principles of recombinant DNA technology include Watson et al., Molecular Biology of the Gene, Volumes I and II, The Benjamin/Cummings Publishing Company, Inc., Menlo Park, Calif. (1987); Darmell et al., Molecular Cell Biology, Scientific American Books, Inc., New York, N.Y. (1986); Lewin, Genes II, John Wiley & Sons, New York, N.Y. (1985); Old, et al., Principles of Gene Manipulation: An Introduction to Genetic Engineering 2d edition, University of California Press, Berkeley, Calif. (1981); Sambrook et al., Molecular Cloning: A Laboratory Manual, Cold Spring Harbor Laboratory, Cold Spring Harbor, N.Y. (1989); and Ausubel et al, Current Protocols in Molecular Biology, Wiley Interscience, N.Y., (1987, 1992). These references are herein entirely incorporated by reference as are the references cited therein.

ASSAYS FOR PLASMIN BINDING AND INHIBITION

Any suitable method may be used to test the compounds of this invention. Scatchard (*Ann NY Acad Sci* (1949) 51:660–669) described a classical method of measuring and analyzing binding which is applicable to protein binding. This method requires relatively pure protein and the ability to distinguish bound protein from unbound.

A second appropriate method of measuring $K_D$ is to measure the inhibitory activity against the enzyme. If the $K_D$ to be measured is in the 1 nM to 1 $\mu$M range, this method requires chromogenic or fluorogenic substrates and tens of micrograms to milligrams of relatively pure inhibitor. For the proteins of this invention, having $K_D$ in the range 5 nM to 50 pM, nanograms to micrograms of inhibitor suffice. When using this method, the competition between the inhibitor and the enzyme substrate can give a measured $K_i$ that is higher than the true $K_i$. Measurement reported here are not so corrected because the correction would be very small and the any correction would reduce the $K_i$. Here, we use the measured $K_i$ as a direct measure of KD.

A third method of determining the affinity of a protein for a second material is to have the protein displayed on a genetic package, such as M13, and measure the ability of the protein to adhere to the immobilized "second material". This method is highly sensitive because the genetic packages can be amplified. We obtain at least semiquantitative values for the binding constants by use of a pH step gradient. Inhibitors of known affinity for the protease are used to establish standard profiles against which other phage-displayed inhibitors are judged. Any other suitable method of measuring protein binding may be used.

Preferably, the proteins of this invention have a $K_D$ for plasmin of at most about 5 nM, more preferably at most about 300 pM, and most preferably 100 pM or less. Preferably, the binding is inhibitory so that $K_i$ is the same as $K_D$. The $K_i$ of QS4 for plasmin is about 2 nM. The $K_i$ of SPI11 for plasmin is about 88 pM.

PHARMACEUTICAL METHODS AND PREPARATIONS

The preferred subject of this invention is a mammal. The invention is particularly useful in the treatment of humans, but is suitable for veternary applications too.

Herein, "protection" includes "prevention", "suppression", and "treatment". "Prevention" involves administration of drug prior to the induction of disease. "Suppression" involves administration of drug prior to the clinical appearance of disease. "Treatment" involves administration of drug after the appearance of disease.

In human and veterinary medicine, it may not be possible to distinguish between "preventing" and "suppressing" since the inductive event(s) may be unknown or latent, or the patient is not ascertained until after the occurrence of the inductive event(s). We use the term "prophylaxis" as distinct from "treatment" to encompass "preventing" and "suppressing". Herein, "protection" includes "prophylaxis". Protection need not by absolute to be useful.

Proteins of this invention may be administered, by any means, systemically or topically, to protect a subject against a disease or adverse condition. For example, administration of such a composition may be by any parenteral route, by bolus injection or by gradual perfusion. Alternatively, or concurrently, administration may be by the oral route. A suitable regimen comprises administration of an effective amount of the protein, administered as a single dose or as several doses over a period of hours, days, months, or years.

The suitable dosage of a protein of this invention may depend on the age, sex, health, and weight of the recipient, kind of concurrent treatment, if any, frequency of treatment, and the desired effect. However, the most preferred dosage can be tailored to the individual subject, as is understood and determinable by one of skill in the art, without undue experimentation by adjustment of the dose in ways known in the art.

For methods of preclinical and clinical testing of drugs, including proteins, see, e.g., Berkow et al, eds., The Merck Manual, 15th edition, Merck and Co., Rahway, N.J., 1987; Goodman et al., eds., Goodman and Gilman's The Pharmacological Basis of Therapeutics, 8th edition, Pergamon Press, Inc., Elnsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985), which references and references cited there are hereby incorporated by reference.

In addition to a protein here disclosed, a pharmaceutical composition may contain pharmaceutically acceptable carriers, excipients, or auxiliaries. See, e.g., Berker, supra, Goodman, supra, Avery, supra and Ebadi, supra.

IN VITRO DIAGNOSTIC METHODS AND REAGENTS

Proteins of this invention may be applied in vitro to any suitable sample that might contain plasmin to measure the plasmin present. To do so, the assay must include a Signal Producing System (SPS) providing a detectable signal that depends on the amount of plasmin present. The signal may be detected visually or instrumentally. Possible signals include production of colored, fluorescent, or luminescent products, alteration of the characteristics of absorption or emission of radiation by an assay component or product, and precipitation or agglutination of a component or product.

The component of the SPS most intimately associated with the diagnostic reagent is called the "label". A label may be, e.g., a radioisotope, a fluorophore, an enzyme, a co-enzyme, an enzyme substrate, an electron-dense compound, or an agglutinable particle. A radioactive isotope can be detected by use of, for example, a $\gamma$ counter or a scintillation counter or by autoradiography. Isotopes which are particularly useful are $^3H$, $^{125}I$, $^{131}I$, $^{35}S$, $^{14}C$, and, preferably, $^{125}I$. It is also possible to label a compound with a fluorescent compound. When the fluorescently labeled compound is exposed to light of the proper wave length, its presence can be detected. Among the most commonly used fluorescent labelling compounds are fluorescein isothiocyanate, rhodamine, phycoerythrin, phycocyanin, allophycocyanin, o-phthaldehyde, and fluorescamine. Alternatively, fluorescence-emitting metals, such as $^{125}Eu$ or other lanthanide, may be attached to the binding protein using such metal chelating groups as diethylenetriaminepentaacetic acid or ethylenediamine-tetraacetic acid. The proteins also can be detectably labeled by coupling to a chemiluminescent compound, such as luminol, isolumino, theromatic acridinium ester, imidazole, acridinium salt, and oxalate ester. Likewise, a bioluminescent compound, such as luciferin, luciferase and aequorin, may be used to label the binding protein. The presence of a bioluminescent protein is determined by detecting the presence of luminescence. Enzyme labels, such as horseradish peroxidase and alkaline phosphatase, are preferred.

There are two basic types of assays: heterogeneous and homogeneous. In heterogeneous assays, binding of the affinity molecule to analyte does not affect the label; thus, to determine the amount of analyte, bound label must be separated from free label. In homogeneous assays, the interaction does affect the activity of the label, and analyte can be measured without separation.

In general, a plasmin-binding protein (PBP) may be used diagnostically in the same way that an antiplasmin antibody is used. Thus, depending on the assay format, it may be used to assay plasmin, or, by competitive inhibition, other substances which bind plasmin.

The sample will normally be a biological fluid, such as blood, urine, lymph, semen, milk, or cerebrospinal fluid, or a derivative thereof, or a biological tissue, e.g., a tissue section or homogenate. The sample could be anything. If the sample is a biological fluid or tissue, it may be taken from a human or other mammal, vertebrate or animal, or from a plant. The preferred sample is blood, or a fraction or derivative thereof.

In one embodiment, the plasmin-binding protein (PBP) is immobilized, and plasmin in the sample is allowed to compete with a known quantity of a labeled or specifically labelable plasmin analogue. The "plasmin analogue" is a molecule capable of competing with plasmin for binding to the PBP, which includes plasmin itself. It may be labeled already, or it may be labeled subsequently by specifically binding the label to a moiety differentiating the plasmin analogue from plasmin. The phases are separated, and the labeled plasmin analogue in one phase is quantified.

In a "sandwich assay", both an insolubilized plasmin-binding agent (PBA), and a labeled PBA are employed. The plasmin analyte is captured by the insolubilized PBA and is tagged by the labeled PBA, forming a tertiary complex. The reagents may be added to the sample in any order. The PBAs may be the same or different, and only one PBA need be a PBP according to this invention (the other may be, e.g., an antibody). The amount of labeled PBA in the tertiary complex is directly proportional to the amount of plasmin in the sample.

The two embodiments described above are both heterogeneous assays. A homogeneous assay requires only that the label be affected by the binding of the PBP to plasmin. The plasmin analyte may act as its own label if a plasmin inhibitor is used as a diagnostic reagent.

A label may be conjugated, directly or indirectly (e.g., through a labeled anti-PBP antibody), covalently (e.g., with SPDP) or noncovalently, to the plasmin-binding protein, to produce a diagnostic reagent. Similarly, the plasmin binding protein may be conjugated to a solid phase support to form a solid phase ("capture") diagnostic reagent. Suitable supports include glass, polystyrene, polypropylene, polyethylene, dextran, nylon, amylases, and magnetite. The carrier can be soluble to some extent or insoluble for the purposes of this invention. The support material may have any structure so long as the coupled molecule is capable of binding plasmin.

In vivo Diagnosic Uses

A Kunitz domain that binds very tightly to plasmin can be used for in vivo imaging. Diagnostic imaging of disease foci was considered one of the largest commercial opportunities for monoclonal antibodies, but this opportunity has not been achieved. Despite considerable effort, only two monoclonal antibody-based imaging agents have been approved. The disappointing results obtained with monoclonal antibodies is due in large measure to:

i) Inadequate affinity and/or specificity;
   ii) Poor penetration to target sites;
   iii) Slow clearance from nontarget sites;
   iv) Immunogenicity (most are murine); and
   v) High production cost and poor stability.

These limitations have led most in the diagnostic imaging field to begin to develop peptide-based imaging agents. While potentially solving the problems of poor penetration and slow clearance, peptide-based imaging agents are unlikely to possess adequate affinity, specificity and in vivo stability to be useful in most applications.

Engineered proteins are uniquely suited to the requirements for an imaging agent. In particular the extraordinary affinity and specificity that is obtainable by engineering small, stable, human-origin protein domains having known in vivo clearance rates and mechanisms combine to provide earlier, more reliable results, less toxicity/side effects, lower production and storage cost, and greater convenience of label preparation. Indeed, it should be possible to achieve the goal of realtime imaging with engineered protein imaging agents. Plasmin-binding proteins, e.g. SPI11, may be useful for localizing sites of internal hemorrhage.

Radio-labelled binding protein may be administered to the human or animal subject. Administration is typically by injection, e.g., intravenous or arterial or other means of administration in a quantity sufficient to permit subsequent dynamic and/or static imaging using suitable radio-detecting devices. The dosage is the smallest amount capable of providing a diagnostically effective image, and may be determined by means conventional in the art, using known radio-imaging agents as guides.

Typically, the imaging is carried out on the whole body of the subject, or on that portion of the body or organ relevant to the condition or disease under study. The radio-labelled binding protein has accumulated. The amount of radio-labelled binding protein accumulated at a given. point in time in relevant target organs can then be quantified.

A particularly suitable radio-detecting device is a scintillation camera, such as a γ camera. The detection device in the camera senses and records (and optional digitizes) the radioactive decay. Digitized information can be analyzed in any suitable way, many of which are known in the art. For example, a time-activity analysis can illustrate uptake through clearance of the radio-labelled binding protein by the target organs with time.

Various factors are taken into consideration in picking an appropriate radioisotope. The isotope is picked: to allow good quality resolution upon imaging, to be safe for diagnostic use in humans and animals, and, preferably, to have a short half-life so as to decrease the amount of radiation received by the body. The radioisotope used should preferably be pharmacologically inert, and the quantities administered should not have substantial physiological effect. The binding protein may be radio-labelled with different isotopes of iodine, for example $^{123}I$, $^{125}I$, or $^{131}I$ (see, for example, U.S. Pat. No. 4,609,725). The amount of labeling must be suitably monitored.

In applications to human subjects, it may be desirable to use radioisotopes other than $^{125}I$ for labelling to decrease the total dosimetry exposure of the body and to optimize the detectability of the labelled molecule. Considering ready clinical availability for use in humans, preferred radio-labels include: $^{99m}Tc$, $^{67}Ga$, $^{68}Ga$, $^{90}Y$, $^{111}In$, $^{113m}In$, $^{123}I$, $^{186}Re$, $^{188}Re$ or $^{211}At$. Radio-labelled protein may be prepared by various methods. These include radio-halogenation by the chloramine-T or lactoperoxidase method and subsequent purification by high pressure liquid chromatography, for example, see Gutkowska et al in "Endocrinology and Metabolism Clinics of America: (1987) 16 (1):183. Other methods of radio-labelling can be used, such as IODO-BEADS™.

A radio-labelled protein may be administered by any means that enables the active agent to reach the agent's site of action in a mammal. Because proteins are subject to digestion when administered orally, parenteral administration, i.e., intravenous subcutaneous, intramuscular, would ordinarily be used to optimize absorption.

Other Uses

The plasmin-binding proteins of this invention may also be used to purify plasmin from a fluid, e.g., blood. For this purpose, the PBP is preferably immobilized on an insoluble support. Such supports include those already mentioned as useful in preparing solid phase diagnostic reagents.

Proteins can be used as molecular weight markers for reference in the separation or purification of proteins. Proteins may need to be denatured to serve as molecular weight markers. A second general utility for proteins is the use of hydrolyzed protein as a nutrient source. Proteins may also be used to increase the viscosity of a solution.

The protein of this invention may be used for any of the foregoing purposes, as well as for therapeutic and diagnostic purposes as discussed further earlier in this specification.

PREPARATION OF PEPTIDES

Chemical polypeptide synthesis is a rapidly evolving area in the art, and methods of solid phase polypeptide synthesis are well-described in the following references, hereby entirely incorporated by reference: (Merrifield, *J Amer Chem Soc* 85:2149–2154 (1963); Merrifield, *Science* 232:341–347 (1986); Wade et al., *Biopolymers* 25:S21–S37 (1986); Fields, *Int J Polypeptide Prot Res* 35:161 (1990); MilliGen Report Nos. 2 and 2a, Millipore Corporation, Bedford, Mass., 1987) Ausubel et al, supra, and Sambrook et al, supra. Tan and Kaiser (*Biochemistry,* 1977, 16:1531–41) synthesized BPTI and a homologue eighteen years ago.

As is known in the art, such methods involve blocking or protecting reactive functional groups, such as free amino, carboxyl and thio groups. After polypeptide bond formation, the protective groups are removed. Thus, the addition of each amino acid residue requires several reaction steps for protecting and deprotecting. Current methods utilize solid phase synthesis, wherein the C-terminal amino acid is covalently linked to an insoluble resin particles that can be filtered. Reactants are removed by washing the resin particles with appropriate solvents using an automated machine. Various methods, including the "tBoc" method and the "Fmoc" method are well known in the art. See, inter alia, Atherton et al., *J Chem Soc Perkin Trans* 1:538–546 (1981) and Sheppard et al., *Int J Polypeptide Prot Res* 20:451–454 (1982).

EXAMPLES

Example 1

Construction of LACI (K1) Library

A synthetic oligonucleotide duplex having NsiI- and MluI-compatible ends was cloned into a parental vector (LACI-K1::III) previously cleaved with the above two enzymes. The resultant ligated material was transfected by electroporation into XLIMR (F⁻) *E. coli* strain and plated on ampicillin (Ap) plates to obtain phage-generating $Ap^R$ colonies. The variegation scheme for Phase 1 focuses on the P1 region, and affected residues 13, 16, 17, 18 and 19. It allowed for $6.6 \times 10^5$ different DNA sequences ($3.1 \times 10^5$ different protein sequences). The library obtained consisted of $1.4 \times 10^6$ independent cfu's which is approximately a two fold representation of the whole library. The phage stock generated from this plating gave a total titer of $1.4 \times 10^{13}$ pfu's in about 3.9 ml, with each independent clone being represented, on average, $1 \times 10^7$ in total and $2.6 \times 10^6$ times per ml of phage stock.

To allow for variegation of residues 31, 32, 34 and 39 (phase II), synthetic oligonucleotide duplexes with MluI- and BstEII-compatible ends were cloned into previously cleaved $R_f$ DNA derived from one of the following
  i) the parental construction,
  ii) the phase I library, or
  iii) display phage selected from the first phase binding to a given target.

The variegation scheme for phase II allows for 4096 different DNA sequences (1600 different protein sequences) due to alterations at residues 31, 32, 34 and 39. The final phase II variegation is dependent upon the level of variegation remaining following the three rounds of binding and elution with a given target in phase I.

The combined possible variegation for both phases equals $2.7 \times 10^8$ different DNA sequences or $5.0 \times 10^7$ different protein sequences. When previously selected display phage are used as the origin of $R_f$ DNA for the phase II variegation, the final level of variegation is probably in the range of $10^5$ to $10^6$.

Example 2

Screening of LACI-K1 Library for Binding to Plasmin

The scheme for selecting LACI-K1 variants that bind plasmin involves incubation of the phage-display library with plasmin-beads (Calbiochem, San Diego, Calif.; catalogue no. 527802) in a buffer (PBS containing 1 mg/ml BSA) before washing away unbound and poorly retained display-phage variants with PBS containing 0.1% Tween 20. The more strongly bound display-phage are eluted with a low pH elution buffer, typically citrate buffer (pH 2.0) containing 1 mg/ml BSA, which is immediately neutralized with Tris buffer to pH 7.5. This process constitutes a single round of selection.

The neutralized eluted display-phage can be either used:

i) to inoculate an $F^+$ strain of *E. coli* to generate a new display-phage stock, to be used for subsequent rounds of selection (so-called conventional screening), or ii) be used directly for another immediate round of selection with the protease beads (so-called quick screening).

Typically, three rounds of either method, or a combination of the two, are performed to give rise to the final selected display-phage from which a representative number are sequenced and analyzed for binding properties either as pools of display-phage or as individual clones.

For the LACI-K1 library, two phases of selection were performed, each consisting of three rounds of binding and elution. Phase I selection used the phase I library (variegated residues 13, 16, 17, 18, and 19) which went through three rounds of binding and elution against plasmin giving rise to a subpopulation of clones. The $R_f$ DNA derived from this selected subpopulation was used to generate the Phase II library (addition of variegated residues 31, 32, 34 and 39). About $5.6 \times 10^7$ independent transformants were obtained. The phase II libraries underwent three further rounds of binding and elution with the same target protease giving rise to the final selectants.

Following two phases of selection against plasmin-agarose beads a representative number (16) of final selection display-phage were sequenced. Table 2 shows the sequences of the selected LACI-K1 domains with the amino acids selected at the variegated positions in upper case. Note the absolute selection of residues $P_{13}$, $A_{16}$, $R_{17}$, $F_{18}$, and $E_{19}$. There is very strong selection for E at 31 and Q at 32. There is no consensus at 34; the observed amino acids are $\{T_3, Y_2, H_2, D, R, A, V_2, I_3,$ and $L\}$. The amino acids having side groups that branch at $C_\beta$ (T, I, and V) are multiply represented and are preferred. At position 39, there is no strong consensus ($G_6, D_3, Q_2, A_2, R, F, E$), but G, D, Q, and A seem to be preferred (in that order).

A separate screening of the LACI-K1 library against plasmin gave a very similar consensus from 16 sequenced selected display-phage. These sequences are shown in Table 3 (selected residues in upper case). These sequences depart from those of Table 2 in that E here predominates at position 19. There is a consensus at 34 ($T_5, V_3, S_3, I_2, L, A, F$) of T, V, or S. Combining the two sets, there is a preference for (in order of preference) T, V, I, S, A, H, Y, and L, with F, D, and R being allowed.

Expression, Purification and Kinetic Analysis

The three isolates QS4, ARFK#1, and ARFK#2 were recloned into a yeast expression vector. The yeast expression vector is derived from pMFalpha8 (KURJ82 and MIYA85). The LACI variant genes were fused to part of the matα 1 gene, generating a hybrid gene consisting of the matα 1 promoter-signal peptide and leader sequence-fused to the LACI variant. The cloning site is shown in Table 24. Note that the correctly processed LACI-K1 variant protein should be as detailed in Table 2 and Table 3 with the addition of residues glu-ala-ala-glu to the N-terminal met (residue 1 in Table 2 and Table 3). Expression in *S. cerevisiae* gave a yield of about 500 μg of protease inhibitor per liter of medium. Yeast-expressed LACI (kunitz domain 1), EPTI and LACI variants: QS4, ARFK#1 and ARFK#2 were purified by affinity chromatography using trypsin-agarose beads.

The most preferred production host is *Pichia pastoris* utilizing the alcohol oxidase system. Others have produced a number of proteins in the yeast *Pichia pastoris*. For example, Vedvick et al. (VEDV91) and Wagner et al. (WAGN92) produced aprotinin from the alcohol oxidase promoter with induction by methanol as a secreted protein in the culture medium at ≈1 mg/ml. Gregg et al. (GREG93) have reviewed production of a number of proteins in *P. pastoris*. Table 1 of GREG93 shows proteins that have been produced in *P. pastoris* and the yields.

Kinetic data

Inhibition of hydrolysis of succinyl-Ala-Phe-Lys-($F_3$Ac) AMC (a methyl coumarin) (Sigma Chemical, St. Louis, Mo.) by plasmin at $2.5 \times 10^{-8}$ M with varying amount of inhibitor were fit to the standard form for a tight-binding substrate by least-squares. Preliminary kinetic analysis of the two ARFK variants demonstrated very similar inhibitory activity to that of the QS4 variant.) These measurements were carried out with physiological amounts of salt (150 mM) so that the affinities are relevant to the action of the proteins in blood.

Table 23 shows that QS4 is a highly specific inhibitor of human plasmin. Phage that display the LACI-K1 derivative QS4 bind to plasmin beads at least 50-times more than it binds to other protease targets.

New Library for Plasmin

A new library of LACI-K1 domains, displayed on M13 gIIIp and containing the diversity shown in Table 5 was made and screened for plasmin binding. Table 6 shows the sequences selected and the consensus. We characterized the binding of the selected proteins by comparing the binding of clonally pure phage to BPTI display phage. Isolates 11, 15, 08, 23, and 22 were superior to BPTI phage. We produced soluble SPI11 (Selected Plasmin Inhibitor#11) and tested its inhibitory activity, obtaining a $K_i$ of 88 pM which is at least two-fold better than BPTI. Thus, we believe that the selectants SPI15, SPI08, and SPI22 are far superior to BPTI and that SPI23 is likely to be about as potent as BPTI. All of the listed proteins are much closer to a human protein amino-acid sequence than is BPTI and so have less potential for immunogenicity.

All references, including those to U.S. and foreign patents or patent applications, and to nonpatent disclosures, are hereby incorporated by reference in their entirety.

TABLE 1

Sequence of whole LACI: (SEQ ID NO. 1)

```
          5          5          5          5          5
  1 MIYTMKKVHA LWASVCLLLN LAPAPLNAds eedeehtiit dtelpplklM
 51 HSFCAFKADD GPCKAIMKRF FFNIFTRQCE EFIYGGCEGN QNRFESLEEC
101 KKMCTRDnan riikttlqqe kpdfCfleed pgiCrgyitr yfynnqtkqC
151 erfkyggClg nmnnfetlee CkniCedgpn gfqvdnygtq lnavnnsltp
201 qstkvpslfe fhgpswCltp adrglCrane nrfyynsvig kCrpfkysgC
251 ggnennftsk qeClraCkkg fiqriskggl iktkrkrkkq rvkiayeeif
301 vkn
```

The signal sequence (1–28) is uppercase and underscored
LACI-K1 is uppercase
LACI-K2 is underscored
LACI-K3 is bold

TABLE 2

Sequence of LACI-K1 and derivatives that bind human plasmin

```
                   1         2         3         4         5
          12345678901234567890123456789012345678901234567890012345678
```

| | | |
|---|---|---|
| LACI-K1 | mhsfcafkaddgpckaimkrfffniftrqceefiyggcegnqnrfesleeckkmctrd | SEQ ID NO. 2 |
| QS1 | mhsfcafkaddgPckARFErfffniftrqcEQfTyggcRgnqnrfesleeckkmctrd | SEQ ID NO. 3 |
| QS4 | mhsfcafkaddgPckARFErfffniftrqcEQfYyggcDgnqnrfesleeckkmctrd | SEQ ID NO. 4 |
| QS7 | mhsfcafkaddgPckARFErfffniftrqcEQfHyggcDgnqnrfesleeckkmctrd | SEQ ID NO. 5 |
| QS8 | mhsfcafkaddgPckARFErfffniftrqcEQfDyggcAgnqnrfesleeckkmctrd | SEQ ID NO. 6 |
| QS9 | mhsfcafkaddgPckARFErfffniftrqcQEfRyggcDgnqnrfesleeckkmctrd | SEQ ID NO. 7 |
| QS13 | mhsfcafkaddgPckARFErfffniftrqcQQfYyggcQgnqnrfesleeckkmctrd | SEQ ID NO. 8 |
| QS15 | mhsfcafkaddgPckARFErfffniftrqcEEfAyggcGgnqnrfesleeckkmctrd | SEQ ID NO. 9 |
| NS2 | mhsfcafkaddgPckARFErfffniftrqcQQfVyggcGgnqnrfesleeckkmctrd | SEQ ID NO. 10 |
| NS4 | mhsfcafkaddgPckARFErfffniftrqcEQfTyggcGgnqnrfesleeckkmctrd | SEQ ID NO. 11 |
| NS6 | mhsfcafkaddgPckARFErfffniftrqcEEfTyggcGgnqnrfesleeckkmctrd | SEQ ID NO. 12 |
| NS9 | mhsfcafkaddgPckARFErfffniftrqcEQfIyggcGgnqnrfesleeckkmctrd | SEQ ID NO. 13 |
| NS11 | mhsfcafkaddgPckARFErfffniftrqcEQfIyggcGgnqnrfesleeckkmctrd | SEQ ID NO. 14 |
| NS12 | mhsfcafkaddgPckARFErfffniftrqcEQfIyggcFgnqnrfesleeckkmctrd | SEQ ID NO. 15 |
| NS14 | mhsfcafkaddgPckARFErfffniftrqcQQfHyggcEgnqnrfesleeckkmctrd | SEQ ID NO. 16 |
| NS15 | mhsfcafkaddgPckARFErfffniftrqcEQfVyggcAgnqnrfesleeckkmctrd | SEQ ID NO. 17 |
| NS16 | mhsfcafkaddgPckARFErfffniftrqcEQfLyggcGgnqnrfesleeckkmctrd | SEQ ID NO. 18 |
| ARFRCON | mhsfcafkaddgPckARFErfffniftrqcEQfiyggcGgnqnrfesleeckkmctrd | SEQ ID NO. 19 |

TABLE 3

Sequence of LACI-K1 and derivatives that bind human plasmin

```
                   1         2         3         4         5
          12345678901234567890123456789012345678901234567890012345678
```

| | | |
|---|---|---|
| LACI-K1 | mhsfcafkaddgpckaimkrfffniftrqceefiyggcegnqnrfesleeckkmctrd | SEQ ID NO. 2 |
| ARFK#1 | mhsfcafkaddgPckARFErfffniftrqcEQfVyggcGgnqnrfesleeckkmctrd | SEQ ID NO. 20 |

TABLE 3-continued

Sequence of LACI-K1 and derivatives that bind human plasmin

| | | |
|---|---|---|
| ARFK#2 | mhsfcafkaddgPckARFErfffniftrqcEEfVyggcGgnqnrfesleeckkmctrd | SEQ ID NO. 21 |
| ARFK#3 | mhsfcafkaddgLckGRFQrfffniftrqcEEfIyggcEgnqnrfesleeckkmctrd | SEQ ID NO. 22 |
| ARFK#4 | mhsfcafkaddgPckARFErfffniftrqcEQfTyggcMgnqnrfesleeckkmctrd | SEQ ID NO. 23 |
| ARFK#5 | mhsfcafkaddgPckARFErfffniftrqcEQfSyggcGgnqnrfesleeckkmctrd | SEQ ID NO. 24 |
| ARFK#6 | mhsfcafkaddgPckARFErfffniftrqcEEfLyggcLgnqnrfesleeckkmctrd | SEQ ID NO. 25 |
| ARFK#7 | mhsfcafkaddgPckARFErfffniftrqcEQfSyggcQgnqnrfesleeckkmctrd | SEQ ID NO. 26 |
| ARFK#8 | mhsfcafkaddgPckARFErfffniftrqcEQfAyggcAgnqnrfesleeckkmctrd | SEQ ID NO. 27 |
| ARFK#9 | mhsfcafkaddgPckARFErfffniftrqcEQfIyggcVgnqnrfesleeckkmctrd | SEQ ID NO. 28 |
| ARFK#10 | mhsfcafkaddgPckARFErfffniftrqcEEfSyggcKgnqnrfesleeckkmctrd | SEQ ID NO. 29 |
| ARFK#11 | mhsfcafkaddgPckARFErfffniftrqcEEfVyggcKgnqnrfesleeckkmctrd | SEQ ID NO. 30 |
| ARFK#12 | mhsfcafkaddgPckASFErfffniftrqcEQfTyggcNgnqnrfesleeckkmctrd | SEQ ID NO. 31 |
| ARFK#13 | mhsfcafkaddgPckASFErfffniftrqcEEfTyggcLgnqnrfesleeckkmctrd | SEQ ID NO. 32 |
| ARFK#14 | mhsfcafkaddgPckARFErfffniftrqcEQfFyggcHgnqnrfesleeckkmctrd | SEQ ID NO. 33 |
| ARFK#15 | mhsfcafkaddgPckARFErfffniftrqcEQfTyggcGgnqnrfesleeckkmctrd | SEQ ID NO. 34 |
| ARFK#16 | mhsfcafkaddgPckARFErfffniftrqcEQfTyggcMgnqnrfesleeckkmctrd | SEQ ID NO. 35 |
| ARFKCO1 | mhsfcafkaddgPckARFErfffniftrqcEQfTyggcGgnqnrfesleeckkmctrd | SEQ ID NO. 36 |
| ARFKCO2 | mhsfcafkaddgPckARFErfffniftrqcEQfVyggcGgnqnrfesleeckkmctrd | SEQ ID NO. 37 |

TABLE 4

Kunitz domains, some of which inhibit plasmin

| Protein identifier | Amino-acid Sequence<br>          1111111111222222222233333333334444444444555555555<br>12345678901234567890123456789012345678901234567890123456789012345678 | Affinity $K_D$ | SEQ ID NO. |
|---|---|---|---|
| QS4 | mhsfcafkaddgPckARFErfffniftrqcEQfYyggcDgnqnrfesleeckkmctrd | 2 nM | SEQ ID NO. 4 |
| NS4 | mhsfcafkaddgPckARFErfffniftrqcEQfTyggcGgnqnrfesleeckkmctrd | (B) | SEQ ID NO. 11 |
| BPTI | RPDFCLEPPYTGPCKARIIRYFYNAKAGLCQTFVYGGCRAKRNNFKSAEDCMRTCGGA | .3nM | SEQ ID NO. 38 |
| Human APP-I | VREVCSEQAETGPCRAMISRWYFDVTEGKCAPFFYGGCGGNRNNFDTEEYCMAVCGSA | 75 pM (KID088)<br>225 nM (DENN94a) | SEQ ID NO. 39 |
| SPI11 | mhsfcafkaETgPcRARFDrWffniftrqceefiyggcegnqnrfesleeckkmctrd | 88 pM | SEQ ID NO. 40 |
| SPI15 | mhsfcafkaESgPcRARFDrWffniftrqceefiyggcegnqnrfesleeckkmctrd | (A) | SEQ ID NO. 41 |
| SPI08 | mhsfcafkaDGgPcRARFErFffniftrqceefiyggcegnqnrfesleeckkmctrd | (A) | SEQ ID NO. 42 |
| SPI23 | mhsfcafkaEGgPcRAKFQrWffniftrqceefiyggcegnqnrfesleeckkmctrd | ~.5 nM | SEQ ID NO. 43 |
| SPI22 | mhsfcafkaDGgPcKGKFPrFffniftrqceefiyggcegnqnrfesleeckkmctrd | >2 nM | SEQ ID NO. 44 |
| SPIcon1 | mhsfcafkaETgPcRAKFDrWffniftrqcEAfVyggcGgnqnrfesleeckkmctrd | | SEQ ID NO. 45 |
| SPI60 | mhsfcafkaETgPcRAKFDrWffniftrqcEPfVYggcEgnqnrfesleeckkmctrd | (B) | SEQ ID NO. 46 |
| SPI59 | mhsfcafkaETgPcRAKFDrWffniftrqcNTfVYggcGgnqnrfesleeckkmctrd | | SEQ ID NO. 47 |
| SPI42 | mhsfcafkaETgPcRGkFDrWffniftrqcQGfVYggcGgnqnrfesleeckkmctrd | | SEQ ID NO. 48 |
| SPI55 | mhsfcafkaEVgPcRAkFDrWffniftrqcHLfTYggcGgnqnrfesleeckkmctrd | | SEQ ID NO. 49 |

TABLE 4-continued

Kunitz domains, some of which inhibit plasmin

| Protein identifier | Amino-acid Sequence<br>          1111111111222222222233333333334444444444555555555<br>12345678901234567890123456789012345678901234567890123456 78 | Affinity $K_D$ | SEQ ID NO. |
|---|---|---|---|
| SPI56 | mhsfcafkaETgPcRGkFDrWffniftrqcAQfVYggcEgnqnrfesleeckkmctrd | | SEQ ID NO. 50 |
| SPI43 | mhsfcafkaETgPcRGkFDrWffniftrqcESfHYggcKgnqnrfesleeckkmctrd | >~4 nM | SEQ ID NO. 51 |
| SPI52 | mhsfcafkaDAgPcRAkFErFffniftrqcEAfLYggcGgnqnrfesleeckkmctrd | | SEQ ID NO. 52 |
| SPI46 | mhsfcafkaDVgPcRAkFErFffniftrqcEAfLYggcEgnqnrfesleeckkmctrd | | SEQ ID NO. 53 |
| SPI51 | mhsfcafkaDAgPcRAkFErFffniftrqcTAfFYggcGgnqnrfesleeckkmctrd | ~.5 nM | SEQ ID NO. 54 |
| SPI54 | mhsfcafkaDSgPcRARFDrWffniftrqcTRfPYggcGgnqnrfesleeckkmctrd | >~4 nM | SEQ ID NO. 55 |
| SPI49 | mhsfcafkaETgPcRAkIPrLffniftrqcEPfIWggcGgnqnrfesleeckkmctrd | | SEQ ID NO. 56 |
| SPI47 | mhsfcafkaDAgPcRAkFErFffniftrqcEEfIYggcEgnqnrfesleeckkmctrd | ~.8 nM | SEQ ID NO. 57 |
| SPI53 | mhsfcafkaETgPcKGSFDrWffniftrqcNVfRYggcRgnqnrfesleeckkmctrd | | SEQ ID NO. 58 |
| SPI41 | mhsfcafkaDAgPcRARFErFffniftrqcDTfLYggcEgnqnrfesleeckkmctrd | (AB) | SEQ ID NO. 59 |
| SPI57 | mhsfcafkaDSgPcKGRFGrLffniftrqcTAfDWggcGgnqnrfesleeckkmctrd | | SEQ ID NO. 60 |
| DPI-1.1.1 | mhsfcafkadTgpcRaRFDrfffniftrqceAfiyggcegnqnrfesleeckkmctrd | (A) | SEQ ID NO. 61 |
| DPI-1.1.2 | mhsfcafkadTgpcRaRFDrfffniftrqceefiyggcegnqnrfesleeckkmctrd | (A) | SEQ ID NO. 62 |
| DPI-1.1.3 | mhsfcafkadAgpcRaRFDrfffniftrqceefiyggcegnqnrfesleeckkmctrd | (A) | SEQ ID NO. 63 |
| DPI-1.1.4 | mhsfcafkadTgpckaRFDrfffniftrqceAfiyggcegnqnrfesleeckkmctrd | (AB) | SEQ ID NO. 127 |
| DPI-1.1.5 | mhsfcafkaddgpckaRFDrfffniftrqceefiyggcegnqnrfesleeckkmctrd | (B) | SEQ ID NO. 128 |
| DPI-1.1.6 | mhsfcafkaddgpckaRFkrfffniftrqceefiyggcegnqnrfesleeckkmctrd | (C) | SEQ ID NO. 129 |
| Human LACI-K2 | KPDFCFLEEDPGICRGYITRYFYNNQTKQCERFKYGGCLGNMNNFETLEECKNICEDG | | SEQ ID NO. 64 |
| DPI-1.2.1 | kpdfcfleedTgPcrgRFDryfynnqtkqceTfIyggcEgnmnnfetleecknicedg | | SEQ ID NO. 65 |
| Human LACI-K3 | GPSWCLTPADRGLCRANENRFYYNSVIGKCRPFKYSGCGGNENNFTSKQECLRACKKG | | SEQ ID NO. 66 |
| DPI-1.3.1 | gpswcltpadTgPcraRFDrfyynsvigkcEpfIyGgcggnennftskqeclrackkg | | SEQ ID NO. 67 |
| Human collagen α3 KuDom | ETDICKLPKDEGTCRDFILKWYYDPNTKSCARFWYGGCGGNENKFGSQKECEKVCAPV | | SEQ ID NO. 68 |
| DPI-2.1 | etdicklpkdTgPcrARFDkwyydpntkscEPfVyggcggnenkfgsqkecekvcapv | | SEQ ID NO. 69 |
| Human TFPI-2 DOMAIN 1 | NAEICLLPLDYGPCRALLLRYYYDRYTQSCRQFLYGGCEGNANNFYTWEACDDACWRI | | SEQ ID NO. 70 |
| DPI-3.1.1 | naeicllpldTgpcraRFDryyydrytqscEqflyggcegnannfytweacddacwri | | SEQ ID NO. 71 |
| Human TFPI-2 DOMAIN 2 | VPKVCRLQV-<br>         SVDDQCEGSTEKYFFNLSSMTCEKFFSGGCHRNR-<br>                                   IENRFPDEATCMGFCAPK | | SEQ ID NO. 72 |
| DPI-3.2.1 | vpkvcrlqvETGPcRgKFekyffnlssmtceTfVYggcEGnrnrfpdeatcmgfcapk | | SEQ ID NO. 73 |
| Human TFPI-2 DOMAIN 3 | IPSFCYSPKDEGLCSANVTRYYFNPRYRTCDAFTYTGCGGNDNNFVSREDCKRACAKA | | SEQ ID NO. 74 |
| DPI-3.3.1 | ipsfcyspkdTgPcRaRFtryyfnpryrtcdaftyGgcggndnnfvsredckracaka | | SEQ ID NO. 75 |
| HUMAN ITI-K1 | KEDSCQLGYSAGPCMGMTSRYFYNGTSMACETFQYGGCMGNGNNFVTEKECLQTCRTV | | SEQ ID NO. 76 |
| DPI-4.1.1 | kedscqlgyEagpcRgKFsryfyngtsmacetfVyggcGgngnnfvtekeclqtcrtv | | SEQ ID NO. 77 |

TABLE 4-continued

Kunitz domains, some of which inhibit plasmin

| Protein identifier | Amino-acid Sequence<br>          1111111111222222222233333333334444444444555555555<br>12345678901234567890123456789012345678901234567890123456789012345678 | Affinity $K_D$ | SEQ ID NO. |
|---|---|---|---|
| HUMAN ITI-K2 | TVAACNLPIVRGPCRAFIQLWAFDAVKGKCVLFPYGGCQGNGNKFYSEKECREYCGVP | | SEQ ID NO. 78 |
| DPI-4.2.1 | tvaacnlpiDTgpcraRFqlwafdavkgkcvlfVyggcqgngnkfysekecreycgvp | | SEQ ID NO. 79 |
| PROTEASE NEXIN-II | VREVCSEQAETGPCRAMISRWYFDVTEGKCAPFFYGGCGGNRNNFDTEEYCMAVCGSA | | SEQ ID NO. 80 |
| DPI-5.1 | vrevcseqaetgpcraRFsrwyfdvtegkcapffyggcggnrnnfdteeycmavcgsa | | SEQ ID NO. 81 |
| DPI-5.2 | vrevcseqaetgpcraRFsrwyfdvtegkcEpfIyggcggnrnnfdteeycmavcgsa | | SEQ ID NO. 82 |
| HKI B9 | LPNVCAFPMEKGPCQTYMTRWFFNFETGECELFAYGGCGGNSNNFLRKEKCEKFCKFT | | SEQ ID NO. 124 |
| DPI-6.1 | lpnvcafpmeTgpcRARFtrwffnfetgecelfayggcggnsnnflrkekcekfckft | | SEQ ID NO. 125 |
| DPI-6.2 | lpnvcafpmeTgpcRARFDrwffnfetgecelfVyggcggnsnnflrkekcekfckft | | SEQ ID NO. 126 |
| DPI-4.2.2 | tvaacnlpivTgpcraRFqlwafdavkgkcvlfpyggcqgngnkfysekecreycgvp | | SEQ ID NO. 130 |
| DPI-4.2.3 | tvaacnlpivTgpcraRFqRwafdavkgkcvlfpyggcqgngnkfysekecreycgvp | | SEQ ID NO. 131 |
| DPI-4.2.4 | tvaacnlpivTgpcraRFqRwafdavkgkcvlfVyggcqgngnkfysekecreycgvp | | SEQ ID NO. 132 |
| DPI-4.2.5 | tvaacnlpiETgpcraRFDRwafdavkgkcETfVyggcGgngnkfysekecreycgvp | | SEQ ID NO. 133 |
| DPI-7.1 | rpdfcleppytgpckarFiryfynakaglcqtfvyggcrakrnnfksaedcmrtcgga | | SEQ ID NO. 134 |
| DPI-7.2 | rpdfcleppytgpcRarFiryfynakaglcqtfvyggcrakrnnfksaedcmrtcgga | | SEQ ID NO. 135 |
| DPI-7.3 | rpdfcleppytgpcRarFiryfynakaglcqtfvyggcGakrnnfksaedcmrtcgga | | SEQ ID NO. 136 |
| DPI-7.4 | rpdfcleppDtgpcRarFDryfynakaglcEtfvyggcGakrnnfksaedcmrtcgga | | SEQ ID NO. 137 |

Under "Affinity", "(A)" means the $K_D$ is likely to be less than that of BPTI (viz. 300 pM), "(B)" means $K_D$ is likely to be less than 2 nM, and "(C)" means that $K_D$ is likely to be less than 20 nM.

TABLE 5 vgDNA for LACI-D1 to vary residues 10, 11, 13, 15, 16, 17, & 19 for plasmin in view of App-I (now known not to be very potent)

```
                                                        N|K
           M    H    S    F    C    A    F    K    A    D|E
           1    2    3    4    5    6    7    8    9   10
   5'- cctcct atgcat|tcc|ttc|tgc|gcc|ttc|aag|gct|RaS-
           |NsiI  |
                                      C|W
                                      F|Y
                                      L|P
                                      Q|H
                                      M|I
                                      N|T
     N|S                    T         S|K
     I|T                    N|K       V|R
     A|G       A|P          I|M       D|A
     D|V  G   S|T   C   K|R A|G   R|S F|I E|G  R
     11   12  13   14  15   16   17   18  19   20
     |RNt|ggt|Nct|tgt|aRa|gSt|aNS|wtc|NNs|cgt|

F|C
    L|W   F    F    N    I    F    T    R
    21    22   23   24   25   26   27   28
    |tKS|ttc|ttc|aac|atc|ttc|acg cgt tccctcc-3'    (SEQ ID NO. 83)
       3'-g aag ttg tag aag tgc gca agggagg-5'      (SEQ ID NO. 84)
       Tm ~ 80° C.          | MluI  |
```

DNA     : 262,144 * 4 = 1,048,576
protein: 143,360 * 4 =   573,440
The amino acid seq has SEQ ID NO. 85.

TABLE 5-continued vgDNA for LACI-D1 to vary residues 10, 11, 13, 15, 16, 17, & 19 for plasmin in view of App-I (now known not to be very potent)

This variegation allows the AppI sequence to appear in the P6-P6' positions.

TABLE 6

LACI-K1 derivatives selected for Plasmin binding

| Ident | 10 | 11 | 12 | 13 | 14 | 15 | 16 | 17 | 18 | 19 | 20 | 21 | DIFFS | Phage Binding | $K_D$ (pM) | SEQ ID NO. |
|---|---|---|---|---|---|---|---|---|---|---|---|---|---|---|---|---|
| Consensus | E | T | G | P | C | R | A | R | F | E | R | W | 0 | | | SEQ ID NO. 88 |
| LACI-K1 | d | d | g | p | c | k | a | i | m | k | r | f | 7 | | | SEQ ID NO. 2 |
| SPI31 | – | – | – | – | – | – | – | – | G | – | – | | 1 | | | SEQ ID NO. 89 |
| SPI11 | – | – | – | – | – | – | – | – | D | – | – | | 1 | 3.2 X | 88 | SEQ ID NO. 40 |
| SPI15 | – | S | – | – | – | – | – | – | D | – | – | | 2 | 2.5 X | | SEQ ID NO. 90 |
| SPI24 | D | – | – | – | – | – | G | – | – | G | – | L | 3 | | | SEQ ID NO. 91 |
| SPI33 | – | – | – | S | – | – | G | – | – | D | – | – | 3 | | | SEQ ID NO. 92 |
| SPI34 | – | V | – | – | – | – | – | – | S | – | P | – | 3 | | | SEQ ID NO. 93 |
| SPI26 | – | – | – | – | – | – | – | – | T | – | P | – F | 3 | | | SEQ ID NO. 94 |
| SPI37 | – | V | – | – | – | – | – | – | S | – | H | – | 3 | | | SEQ ID NO. 95 |
| SPI32 | D | – | – | – | – | – | – | – | S | – | G | – | 3 | | | SEQ ID NO. 96 |
| SPI12 | – | – | – | – | – | – | – | G | M | – | P | – | 3 | | | SEQ ID NO. 97 |
| SPI36 | – | G | – | – | – | – | – | – | – | N | – | F | 3 | | | SEQ ID NO. 98 |
| SPI08 | D | G | – | – | – | – | – | – | – | – | – | F | 3 | 2.6 X | | SEQ ID NO. 42 |
| SPI38 | – | – | – | – | – | – | – | – | I | S | – | F | 3 | | | SEQ ID NO. 99 |
| SPI18 | – | G | – | – | – | – | – | – | K | – | – | F | 3 | | | SEQ ID NO. 100 |
| SPI23 | – | G | – | – | – | – | – | – | K | – | Q | – | 3 | 1.25 X | | SEQ ID NO. 43 |
| SPI35 | D | S | – | A | – | – | G | – | – | – | – | – | 4 | | | SEQ ID NO. 101 |
| SPI02 | D | S | – | – | – | – | G | – | – | – | – | F | 4 | 0.83 X | | SEQ ID NO. 102 |
| SPI25 | D | – | – | – | – | – | – | – | S | – | P | –L | 4 | | | SEQ ID NO. 103 |
| SPI17 | – | V | – | – | – | – | – | – | I | Q | – | F | 4 | 0.09 X | | SEQ ID NO. 104 |
| SPI05 | – | S | – | – | – | – | – | – | K | –A | – | F | 4 | 0.64 X | | SEQ ID NO. 105 |
| SPI13 | – | G | – | – | – | – | – | – | K | –A | – | F | 4 | | | SEQ ID NO. 106 |
| SPI07 | D | – | – | S | – | – | – | – | K | I | – | – | 4 | | | SEQ ID NO. 107 |
| SPI03 | D | S | – | – | – | K | – | – | – | D | – | – | 4 | 0.48 | | SEQ ID NO. 108 |
| SPI06 | D | G | – | – | – | K | G | – | – | – | – | – | 4 | | | SEQ ID NO. 109 |
| SPI16 | – | V | – | A | – | K | G | – | – | H | – | – | 5 | 0.22 X | | SEQ ID NO. 110 |
| SPI04 | D | G | – | – | – | – | – | – | S | – | P | – F | 5 | | | SEQ ID NO. 111 |
| SPI01 | D | S | – | A | – | – | – | M | –H | – | F | | 6 | 0.25 X | | SEQ ID NO. 112 |
| SPI14 | D | S | –A | – | – | – | K | – | R | – | – | | 5 | | | SEQ ID NO. 113 |
| SPI28 | D | S | – | T | – | K | – | – | – | P | – | F | 6 | | | SEQ ID NO. 114 |

TABLE 6-continued

LACI-K1 derivatives selected for Plasmin binding

| Ident | 10 | 11 | 12 | 13 | 14 | 15 | 16 | 17 | 18 | 19 | 20 | 21 | DIFFS | Phage Binding | $K_D$ (pM) | SEQ ID NO. |
|---|---|---|---|---|---|---|---|---|---|---|---|---|---|---|---|---|
| SPI27 | – | – | – | – | – | K | G | K | I | A | – | F | 6 | | | SEQ ID NO. 115 |
| SPI21 | D | S | – | A | – | K | G | K | – | – | – | – | 6 | 0.38 X | | SEQ ID NO. 116 |
| SPI22 | D | G | – | – | – | K | G | K | – | P | – | F | 7 | 2.0 X | | SEQ ID NO. 44 |

"Diffs" is the number of differences from the Concensus.
"Phage Binding" is the binding of phage that display the named protein relative to binding of phage that display BPTI.

TABLE 7

Variation of Residues 31, 32, 34, and 39

```
                         T   R   Q   C
            5'-cctcct|acg|cgt|cag|tgc|-
                     | MluI  |
      F|S F|S
      Y|C Y|C
      L|P L|P       G
      H|R H|R       N|D
      W|I W|I       H|R
      T|M T|M       Y|C
      N|K N|K       A|V
      V|A V|A       I|T
      D|G D|G     S|P   C                   E|G
      E|Q E|Q F F|L Y|W G   G   C   K|R G   N   Q
      31  32  33 34    35  36  37  38  39 40  41  42
      |NNS|NNS|ttc|NNt|tRS|ggt|tgt|RRg|ggt|aac|cag|-
                                 | BstEII | gtcgtgctctttagcacgacctg-3'     (SEQ ID NO. 86)
```

The amino acid sequence has SEQ ID NO. 87.
The EcoRI site is erased; thus, cleavage with EcoRI can be used o eliminate (or at least greatly reduce) parental DNA.
There are 262,144 DNA sequences and 72,000 protein sequences.

TABLE 8

Selectants for plasmin binding with variegation of second loop

| Id | 111111111122<br>012345678901 | 3333333334<br>1234567890 | # Diffs<br>Cl C K1 | SEQ ID NO. |
|---|---|---|---|---|
| Con1 | ETgPcRAKFDrW | EAfVYggcGg | 10 | SEQ ID NO. 45 |
| SPI47 | DA-------E-F | -E-I----E- | 7 (5) 5 | SEQ ID NO. 57 |
| SPI51 | DA-------E-F | T--F------ | 6 (4) 9 | SEQ ID NO. 54 |
| SPI52 | DA-------E-F | ---L------ | 5 (3) 8 | SEQ ID NO. 52 |
| SPI46 | DV-------E-F | ---L----E- | 6 (3) 7 | SEQ ID NO. 53 |
| SPI41 | DA-----R-E-F | DT-L----E- | 9 (6) 8 | SEQ ID NO. 59 |
| SPI42 | ------G----- | QG-------- | 3 (3) 12 | SEQ ID NO. 48 |
| SPI43 | ------G----- | -S-H----K- | 4 (4) 11 | SEQ ID NO. 51 |
| SPI56 | ------G----- | AQ------E- | 4 (3) 11 | SEQ ID NO. 50 |
| SPI59 | ------------ | NT-------- | 2 (2) 11 | SEQ ID NO. 47 |

TABLE 8-continued

Selectants for plasmin binding with variegation of second loop

| Id | 111111111122<br>012345678901 | 3333333334<br>1234567890 | # Diffs<br>C1 C K1 | |
|---|---|---|---|---|
| SPI60 | ------------ | -P------E- | 2 (1) 9 | SEQ ID NO. 46 |
| SPI55 | -V---------- | HL-T------ | 4 (4) 11 | SEQ ID NO. 49 |
| SPI49 | --------IP-L | -P-IW----- | 6 (6) 10 | SEQ ID NO. 56 |
| SPI57 | DS---KGR-G-L | T--DW----- | 10 (8) 11 | SEQ ID NO. 60 |
| SPI53 | -----KGS---- | NV-R----R- | 7 (7) 11 | SEQ ID NO. 58 |
| SPI54 | DS-----R---- | TR-P------ | 6 (4) 10 | SEQ ID NO. 55 |
| SPI11 | -------R---- | eefiyggceg | [1] (4) 7 | SEQ ID NO. 40 |
| LACI1 | ddgpckaimkrf | eefiyggceg | 10 (7) 0 | SEQ ID NO. 2 |

| SPI11<br>Highly<br>Superior | <BPTI<br>very<br>potent | <SPI23 ≈ SPI51<SPI47 | <QS4<br>potent | <SPI22<SPI54<SPI43 |

In the table, "-" means that the protein has the consensus (Con1) type. Con1 contains the most common type at each position; amino acids shown in Con1 were not varied. Four positions (10, 31, 34, and 39) showed significant toleration for a second type, leading to 15 subsidiary consensus sequences: Con2-Con16. The column "#Diffs" shows the number of differences from CON1 under "C1", the differences with the closest of Con1-Con16 under "C", and the differences from LACI-K1 under "K1". SPI11 was selected from a library in which residues 31-39 were locked at the wild-type.

TABLE 9

Conservative and Semiconservative substitutions

| Initial AA type | Category | Conservative substitution | Semi-conservative substitution |
|---|---|---|---|
| A | Small non-polar or slightly polar | G, S, T | N, V, P, (C) |
| C | free SH | A, M, L, V, I | F, G |
| | disulfide | nothing | nothing |
| D | acidic, hydrophilic | E, N, S, T, Q | K, R, H, A |
| E | acidic, hydrophilic | D, Q, S, T, N | K, R, H, A |
| F | aromatic | W, Y, H, L, M | I, V, (C) |
| G | Gly-only conformation | nothing | nothing |
| | "normal" conformation | A, S, N, T | D, E, H, I, K, L, M, Q, R, V |
| H | amphoteric aromatic | Y, F, K, R | L, M, A, (C) |
| I | aliphatic, branched β carbon | V, L, M, A | F, Y, W, G (C) |
| K | basic | R, H | Q, N, S, T, D, E, A |
| L | aliphatic | M, I, V, A | F, Y, W, H, (C) |
| M | hydrophobic | L, I, V, A | Q, F, Y, W, (C), (R), (K), (E) |
| N | non-polar hydrophilic | S, T, (D), Q, A, G, (E) | K, R |
| P | inflexible | V, I | A, (C), (D), (E), F, H, (K), L, M, N, Q, (R), S, T, W, Y |
| Q | aliphatic plus amide | N, E, A, S, T, D | M, L, K, R |
| R | basic | K, Q, H | S, T, E, D, A, |
| S | hydrophilic | A, T, G, N | D, E, R, K |
| T | hydrophilic | A, S, G, N, V | D, E, R, K, I |
| V | aliphatic, branched β carbon | I, L, M, A, T | P, (C) |
| W | aromatic | F, Y, H | L, M, I, V, (C) |
| Y | aromatic | F, W, H | L, M, I, V, (C) |

Changing from A, F, H, I, L, M, P, V, W, or Y to C is semiconservative if the new cysteine remains as a free thiol.
Changing from M to E, R, K is semiconservative if the ionic tip of the new side group can reach the protein surface while the methylene groups make hydrophobic contacts.
Changing from P to one of K, R, E, or D is semiconservative if the side group is on or near the surface of the protein.

TABLE 10

Plasmin-inhibiting Kunitz domain derivatives of LACI-K1

| Posi- | Consensus #1 | | Consensus #2 | | Consensus #3 | | Consensus #4 | |
|---|---|---|---|---|---|---|---|---|
| tion | Type | Status | Type | Status | Type | Status | Type | Status |
| 10 | D | fixed | D | fixed | E/D | S-S | D/E | S-S |
| 11 | D | fixed | D | fixed | T/S | G-S | T/A | G-S |
| 12 | G | fixed | G | fixed | G | fixed | G | fixed |
| 13 | P | Abs-S | P | VS-S | P | VS-S | P | Abs-S |
| 14 | C | fixed | C | fixed | C | fixed | C | fixed |
| 15 | K | fixed | K | fixed | R | S-S | R | S-S |
| 16 | A | Abs-S | A | Abs-S | A | VS-S | A | S-S |
| 17 | R | Abs-S | R | VS-S | R/K | S-S | K | S-S |
| 18 | F | Abs-S | F | Abs-S | F | VS-S | F | VS-S |
| 19 | E | Abs-S | E | Abs-S | E/P/D | S-S | D/E | VS-S |
| 20 | R | fixed | R | fixed | R | fixed | R | fixed |
| 21 | F | fixed | F | fixed | W/F | weak-Sel | W/F | weak-Sel |

TABLE 10-continued

Plasmin-inhibiting Kunitz domain derivatives of LACI-K1

| Posi-tion | Consensus #1 Type | Status | Consensus #2 Type | Status | Consensus #3 Type | Status | Consensus #4 Type | Status |
|---|---|---|---|---|---|---|---|---|
| 31 | E | S-S | E | S-S | E | fixed | E/T | G-S |
| 32 | Q | G-S | Q | G-S | E | fixed | A/T | Strong for no charge weak for type |
| 33 | F | fixed | F | fixed | F | fixed | F | fixed |
| 34 | — | no | T/S | weak | fixed | V/L | | Weak |
| 35 | Y | fixed | Y | fixed | Y | fixed | Y | S-S |
| 39 | — | no consensus | G | weak Sel. | E | fixed | G/E | some-Sel. |

Abs-S Absolute Selection
S-S Strong Selection
VS-S Very Strong Selection
G-S Good Selection

TABLE 11

High Specificity Designed Plasmin Inhibitors

```
                Sequence
                         1111111111222222222233333333334444444444555555555
        Ident     123456789012345678901234567890123456789012345678         SEQ ID NO.

SPI11     mhsfcafkaETgPcRARFDrWffniftrqceefiyggcegnqnrfesleeckkmctrd   SEQ ID NO. 40

SPI11-R15A   mhsfcafkaETgPcAARFDrWffniftrqceefiyggcegnqnrfesleeckkmctrd   SEQ ID NO. 117

SPI11-R15G   mhsfcafkaETgPcGARFDrWffniftrqceefiyggcegnqnrfesleeckkmctrd   SEQ ID NO. 118

SPI11-R15N-    mhsfcafkaETgPcNARFDrWffniftrqceAfiyggcegnqnrfesleeckkmctrd   SEQ ID NO. 117
        E32A
```

TABLE 12

```
     vgDNA for LACI-D1 to vary residues 10, 11, 12, 13,
       14, 15, 16, 17, 19, 20, 21, 37, 38, and 39 for
              plasmin in view of App-I and SPI11
                  M    H    S    F    C    A    F    K    A    D|E
                  1    2    3    4    5    6    7    8    9    10
         5'-cctcct atgcat|tcc|ttc|tgc|gcc|ttc|aag|gct|GaS|
                   |NsiI   |

Y|L  F|S  F|S
                F|S  Y|C  Y|C
                C|P  L|P  L|P
                H|R  H|R  H|R
                I|T  I|T  I|T       N|S
                N|V  N|V  N|V       I|T          V|D
              S|P  A|D  A|D  A|D    V|D          A|E
              T|A    G    G    G    K|R   A|G   R|K    F      G    R|Q
              11   12   13   14    15    16    17   18    19   20
             |NCt|NNt|NNt|NNt|aRa|RNt|aRa|ttc|gNS|cRt|

F|C
             L|W    F    F    N    I    F    T    R    Q    C
             21    22   23   24   25   26   27   28   29   30
             |tKS|ttc|ttc|aac|atc|ttc|acg|cgt|cag|tgc|-3'
             3'-|aag aag ttg tag aag tgc gca gtc acg-
                                           | MluI   |
```

TABLE 12-continued vgDNA for LACI-D1 to vary residues 10, 11, 12, 13, 14, 15, 16, 17, 19, 20, 21, 37, 38, and 39 for plasmin in view of App-I and SPI11

```
                   F|S   F|S
                   Y|C   Y|L
                   L|P   P|H  I|M
                   H|R   R|I  T|N
                   I|T   T|N  K|S
                   N|V   V|A  R|V
                   A|D   D|G  A|E
  E   A   F   V  Y  G   G    C   G|D  G   N   Q
  31  32  33  34 35 36  37   38  39   40  41  42
  Cag Cct tte Ctt tac ggt NNt NNt RNS  ggt aac cag
  ctc cga aag caa atg cca nna  nna yns cca ttg gtc cctcctcc-5'
                                      | BstEII |
```

First (top) strand of DNA has SEQ ID NO. 120.
Second (bottom) strand of DNA has SEQ ID NO. 121.
The amino-acid sequence has SEQ ID NO. 122.
The top strand for codons 31–42 (shown ~~stricken~~ )
need not be synthesized, but is produced by PCR
from the strands shown.

There are 1|37 × 10$^{11}$ DNA sequences that encode
4.66 × 10$^{10}$ amino-acid sequences.

TABLE 14

Definition of a Kunitz Domain (SEQ ID NO. 123)

```
         1         2         3         4         5
12345678901234567890123456789012345678901234567 8
xxxxCxxxxxxGxCxxxxxxxXXXxxxxxxCxxFxXXGCxXxxXxXxxxxxCxxxCxxx
```

Where:
X1, X2, X3, X4, X58, X57, and X56 may be absent,
X21 = Phe, Tyr, Trp,
X22 = Tyr or Phe,
X23 = Tyr or Phe,
X35 = Tyr or Trp,
X36 = Gly or Ser,
X40 = Gly or Ala,
X43 = Asn or Gly, and
X45 = Phe or Tyr

TABLE 15

Substitutions to confer high affinity for plasmin on KuDoms

| Position | Allowed types | Position | Allowed types |
|---|---|---|---|
| 10 | Asp Glu, Tyr | 20 | Arg |
| 11 | Thr, Ala, Ser, Val, Asp | 21 | Phe, Trp, Tyr |
| 12 | Gly | 31 |

TABLE 16

Summary of Sequences selected from First LACI-K1 library for binding to Plasmin

| BPTI # (BPTI type) | (LACI-K1) | Residues Allowed in Library | Preferred Residues |
|---|---|---|---|
| 13 (P) | P | LHPR | PL |
| 16 (A) | A | AG | AG |
| 17 (R) | I | FYLHINA SCPRTVD G | RS |
| 18 (I) | M | all | F |
| 19 (I) | K | LWQMKAG SPRTVE | EQ |
| 31 (Q) | E | EQ | EQ |
| 32 (T) | E | EQ | QE |
| 34 (V) | I | all | TYHDRAVILSF |
| 39 (R) | E | all | GADRQFEMLVKNH |

TABLE 17

Distribution of sequences selected from first library

| Position | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 13 | x | x | x | x | x | x | 0 | x | x | 1 | x | x | 31* | x | 0 | x | x | x | x | x |
| 16 | 31* | x | x | x | x | 1 | x | x | x | x | x | x | x | x | x | x | x | x | x | x |
| 17 | 0 | 0 | 0 | x | 0 | 0 | 0 | 0* | x | 0 | x | 0 | 0 | x | 30 | 2 | 0 | 0 | x | 0 |
| 18 | 0 | 0 | 0 | 0 | 32 | 0 | 0 | 0 | 0 | 0 | 0* | 0 | 0 | 0 | 0 | 0 | 0 | 0 | 0 | 0 |
| 19 | 0 | x | x | 31 | x | 0 | x | x | 0* | 0 | 0 | x | 0 | 1 | 0 | 0 | 0 | 0 | 0 | x |
| 31 | x | x | x | 28* | x | x | x | x | x | x | x | x | x | 4 | x | x | x | x | x | x |
| 32 | x | x | x | 9* | x | x | x | x | x | x | x | x | x | 23 | x | x | x | x | x | x |
| 34 | 2 | 0 | 1 | 0 | 1 | 0 | 2 | 5* | 0 | 2 | 0 | 0 | 0 | 0 | 1 | 3 | 8 | 5 | 0 | 2 |
| 39 | 3 | 0 | 3 | 2* | 1 | 10 | 1 | 0 | 2 | 2 | 2 | 1 | 0 | 3 | 1 | 0 | 0 | 1 | 0 | 0 |

TABLE 18

Distribution of amino-acid types at varied residues in proteins selected for plasmin binding from third library

| Position | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 10 | x | x | 7* | 8 | x | x | x | x | 0 | x | x | 0 | x | x | x | x | x | x | x | x |
| 11 | 4 | x | 0* | x | x | 0 | x | 0 | x | x | x | 0 | x | x | x | 2 | 7 | 2 | x | x |
| 13 | 0 | x | x | x | x | x | x | x | x | x | x | x | 15* | x | x | 0 | 0 | x | x | x |
| 15 | x | x | x | x | x | x | x | x | 2* | x | x | x | x | x | 13 | x | x | x | x | x |
| 16 | 10* | x | x | x | x | 5 | x | x | x | x | x | x | x | x | x | x | x | x | x | x |
| 17 | x | x | x | x | x | x | x | 0* | 11 | x | x | x | 0 | x | 3 | 1 | 0 | x | x | x |
| 18 | x | x | x | x | 14 | x | x | 1 | x | x* | x | x | x | x | x | x | x | x | x | x |
| 19 | 0 | 0 | 8 | 5 | 0 | 1 | 0 | 0 | 0* | 0 | 0 | 0 | 1 | 0 | 0 | 0 | 0 | 0 | 0 | 0 |
| 21 | x | 0 | x | x | 5* | x | x | x | x | 2 | x | x | x | x | x | x | x | 8 | x | x |
| 31 | 1 | 0 | 1 | 6* | 0 | 0 | 1 | 0 | 0 | 0 | 0 | 2 | 0 | 3 | 0 | 0 | 3 | 0 | 0 | 0 |
| 32 | 4 | 0 | 0 | 1* | 0 | 1 | 0 | 0 | 1 | 0 | 0 | 2 | 1 | 1 | 1 | 2 | 1 | 0 | 0 |
| 34 | 0 | 0 | 1 | x | 1 | 0 | 1 | 2* | x | 3 | x | 0 | 1 | x | 1 | 0 | 1 | 4 | x | 0 |
| 35 | x | 0 | x | x | x | x | x | x | x | x | x | x | x | x | x | x | x | 2 | 13* |
| 39 | x | x | x | 5* | x | 8 | x | x | 1 | x | x | x | x | x | 1 | x | x | x | x | x |

TABLE 23

Specificity Results Obtained with KuDoms Displayed on gIIIp of M13

| KuDom Displayed | Target | | | | |
|---|---|---|---|---|---|
| | Plasmin | Thrombin | Kallikrein | Trypsin | Trypsin, 2 washes |
| LACI-K1 | 1.0 | 1.0 | 1.0 | 1.0 | 1.0 |
| QS4 | 52. | 0.7 | 0.9 | 4.5 | 0.5 |
| BPTI | 88. | 1.1 | 1.7 | 0.3 | 0.8 |

LACI-K1 phage for each Target was taken as unit binding and the other display phage are shown as relative binding. BPTI::III phage are not easily liberated from trypsin.

TABLE 24

Mat α S. cerevisiae expression vectors:

Matα1 (Mfα8)
```
            K   R   P   R
5'- . . . |AAA|AAG|CCT|CGA|G . . . -3'
          |  StuI  |
              |  XhoI  |
```

Matα2 (after introduction of a linker into cut DNA)
```
     K   R   E   A   A   E   P   W   G   A   .   .   L   E
5'|AAA|AAG|GAA|GCG|GCC|GAG|CCA|TGG|GGC|GCC|TAA|TAG|CTC|GAG|3'
           |  EagI  |    |  StyI  |  KasI  |      |  XhoI  |
```

Matα-LACI-KI
```
               a   b   c   d   1   2   3   4   5   6   7   8
     K   R   E   A   A   E   M   H   S   F   C   A   F   K
5'|AAA|AGG|GAA|GCG|GCC|GAG|atg|cat|tcc|tcc|tgc|gct|ttc|aaa|
           |  EagI  |    |  NsiI  |

9   10  11  12  13  14  15  16  17  18  19  20
      A   D   D   G   P   C   K   A   I   M   K   R
     |gct|gat|gaC|ggT|ccG|tgt|aaa|gct|atc|atg|aaa|cgt|
              |  RsrII  |             |  BspHI|

21  22  23  24  25  26  27  28  29  30
      F   F   F   N   I   F   T   R   Q   C
     |ttc|ttc|ttc|aac|att|ttc|acG|cgt|cag|tgc|
                              |  MluI  |

31  32  33  34  35  36  37  38  39  40  41  42
      E   E   F   I   Y   G   G   C   R   G   N   Q
     |gag|gaA|ttC|att|tac|ggt|ggt|tgt|gaa|ggt|aac|cag|
      |  EcoRI  |                     |  BstEII  |

43  44  45  46  47  48  49  50
          N   R   F   E   S   L   E   E
         |aac|cgG|ttc|gaa|tct|ctA|gag|gaa|
              |  BstBI  |  XbaI  |
         |  AgeI  |

51  52  53  54  55  56  57  58  59  60
  C   K   K   M   C   T   R   D   G   A
|tgt|aag|aag|atg|tgc|act|cgt|gac|ggc|gcc|TAA|TAG|CTC|GAG|-3'
                              |  KasI  |    |  XhoI  |
```

We expect that Matα pre sequence is cleaved before GLU$_a$-ALA$_b$-

CITATIONS

ADEL86: Adelman et al., *Blood* (1986) 68(6)1280–1284.
ANBA88: Anba et al., *Biochimie* (1988) 70(6)727–733.
AUER88: Auerswald et al., *BioChem Hoppe-Seyler* (1988), 369(Supplement):27–35.
BANE90: Baneyx & Georgiou, *J Bacteriol* (1990) 172(1) 491–494.
BANE91: Baneyx & Georgiou, *J Bacteriol* (1991) 173(8) 2696–2703.
BROW91: Browne et al., *GeneBank* entry M74220.
BROZ90: Broze et al., *Biochemistry* (1990) 29:7539–7546.
COLM87: Colman et al., Editors, Hemostasis and Thrombosis, Second Edition, 1987, J. B. Lippincott Company, Philadelphia, Pa.
DENN94a: Dennis & Lazarus, *J Biological Chem* (1994) 269:22129–22136.
DENN94b: Dennis & Lazarus, *J Biological Chem* (1994) 269:22137–22144.

EIGE90: Eigenbrot et al., *Protein Engineering* (1990), 3(7) 591–598.
ELLI92: Ellis et al., *Ann NY Acad Sci* (1992)667:13–31.
FIDL94: Fidler & Ellis, *Cell* (1994) 79:185–188.
FRAE89: Fraedrich et al., *Thorac Cardiovasc Surg* (1989) 37(2)89–91.
GARD93: Gardell, *Toxicol Pathol* (1993) 21(2)190–8.
GIRA89: Girard et al., *Nature* (1989), 338:518–20.
GIRA91: Girard et al., *J. BIOL. CHEM.* (1991) 266:5036–5041.
GREG93: Gregg et al., *Bio/Technology* (1993) 11:905–910.
HOOV93: Hoover et al., *Biochemistry* (1993) 32:10936–43.
HYNE90: Hynes et al., *Biochemistry* (1990), 29:10018–10022.
KIDO88: Kido et al., *J Biol Chem* (1988), 263:18104–7.
KIDO90: Kido et al., *Biochem & Biophys Res Comm* (1990), 167(2)716–21.
KURJ82: Kurjan and Herskowitz, *Cell* (1982) 30:933–943.
LASK80: Laskowski & Kato, *Ann Rev Biochem* (1980), 49:593–626.
LEAT91: Leatherbarrow & Salacinski, *Biochemistry* (1991) 30(44)10717–21.
LOHM93: Lohmann & J Marshall, *Refract Corneal Surg* (1993) 9(4)300–2.
LUCA83: Lucas et al., *J Biological Chem* (1983) 258(7) 4249–56.
MANN87: Mann & Foster, Chapter 10 of COLM87.
MIYA85: Miyajima et al., *Gene* (1985) 37:155–161.
NEUH89: Neuhaus et al., *Lancet* (1989) 2(8668)924–5.
NOVO89: Novotny et al., *J. BIOL. CHEM.* (1989) 264:18832–18837.
OREI94: O'Reilly et al., *Cell* (1994) 79:315–328.
PARK86: Park & Tulinsky, *Biochemistry* (1986) 25(14) 3977–3982.
PUTT89: Putterman, *Acta Chir Scand* (1989) 155(6–7)367.
ROBB87: Robbins, Chapter 21 of COLM87.
SCHE67: Schechter & Berger. *Biochem Biophys Res Commun* (1967) 27:157–162.
SCHE68: Schechter & Berger. *Biochem Biophys Res Commun* (1968) 32:898–902.
SCHN86: Schnabel et al., *Biol Chem Hoppe-Seyler* (1986), 367:1167–76.
SHER89: Sheridan et al., *Dis Colon Rectum* (1989) 32(6) 505–8.
SPRE94: Sprecher et al., *Proc Natl Acad Sci USA* 91:3353–3357 (1994)
VAND92: van Dijl et al., *EMBO J* (1992) 11(8)2819–2828.
VARA83: Varadi & Patthy, *Biochemistry* (1983) 22:2440–2446.
VARA84: Varadi & Patthy, *Biochemistry* (1984) 23:2108–2112.
VEDV91: Vedvick et al., *J Ind Microbiol* (1991) 7:197–201.
WAGN92: Wagner et al., *Biochem Biophys Res Comm* (1992) 186:1138–1145.
WUNT88: Wun et al., *J. BIOL. CHEM.* (1988) 263:6001–6004.

What is claimed is:

1. An isolated protein that inhibits plasmin comprising a Kunitz domain having the formula:

Xaa1-Xaa2-Xaa3-Xaa4-Cys-Xaa6-Xaa7-Xaa8-Xaa9-Xaa10-

Xaa11-Gly-Xaa13-Cys-Xaa15-Xaa16-Xaa17-Xaa18-Xaa19-

Arg-Xaa21-Xaa22-Xaa23-Xaa24-Xaa25-Xaa26-Xaa27-

Xaa28-Xaa29-Cys-Xaa31-Xaa32-Phe-Xaa34-Xaa35-Xaa36-

Gly-Cys-Xaa39-Xaa40-Xaa41-Xaa42-Xaa43-Xaa44-Xaa45-

Xaa46-Xaa47-Xaa48-Xaa49-Xaa50-Cys-Xaa52-Xaa53-

Xaa54-Cys-Xaa56-Xaa57-Xaa58, wherein

Xaa1, Xaa2, Xaa3, Xaa4, Xaa56, Xaa57 or Xaa58 may be absent;

Xaa10 is selected from Asp, Glu, Tyr and Gln;

Xaa11 is selected from Thr, Ala, Ser, Val and Asp;

Xaa13 is selected from Pro, Leu and Ala;

Xaa15 is selected from Lys and Arg;

Xaa16 is selected from Ala and Gly;

Xaa17 is selected from Arg, Lys and Ser;

Xaa18 is selected from Phe and Ile;

Xaa19 is selected from Glu, Gln, Asp, Pro, Gly, Ser and Ile;

Xaa21 is selected from Phe, Tyr and Trp;

Xaa22 is selected from Tyr and Phe;

Xaa23 is selected from Tyr or Phe;

Xaa31 is selected from Asp, Glu, Thr, Val, Gln and Ala;

Xaa32 is selected from Thr, Ala, Glu, Pro and Gln;

Xaa34 is selected from Val, Ile, Thr, Leu, Phe, Tyr, His, Asp, Ala and Ser;

Xaa35 is selected from Tyr and Trp;

Xaa36 is selected from Gly and Ser;

Xaa39 is selected from Glu, Gly, Asp, Arg, Ala, Gln, Leu, Lys and Met;

Xaa40 is selected from Gly and Ala;

Xaa43 is selected from Asn and Gly; and

Xaa45 is selected from Phe and Tyr.

2. A protein according to claim 1, wherein Xaa1, Xaa2, Xaa3, Xaa4, Xaa56, Xaa57 or Xaa58 may be absent; Xaa 10 is selected from Asp and Glu; Xaa11 is selected from Thr, Ala and Ser; Xaa13 is Pro; Xaa 15 is Arg; Xaa16 is Ala; Xaa17 is Arg; Xaa18 is Phe; Xaa19 is selected from Glu and Asp; Xaa 21 is selected from Phe and Trp; Xaa22 is selected from Tyr and Phe; Xaa23 is selected from Tyr or Phe; Xaa31 is selected from Asp and Glu; Xaa32 is selected from Thr, Ala and Glu; Xaa34 is selected from Val, Ile and Thr; Xaa35 is Tyr; Xaa36 is Gly; Xaa39 is selected from Glu, Gly and Asp; Xaa40 is selected from Gly and Ala; Xaa43 is selected from Asn and Gly; and Xaa45 is selected from Phe and Tyr.

3. A protein according to claim 1, wherein the sequence of said Kunitz domain is selected from the group comprising SPI11 (SEQ ID NO:40), SPI15 (SEQ ID NO:41), SPI08 (SEQ ID NO:42), SPI23 (SEQ ID NO:43), SPI47 (SEQ ID NO:57), QS4(SEQ ID NO:4), NS4 (SEQ ID NO:11), Human LACI-K2 (SEQ ID NO:64), Human LACI-K3 (SEQ ID NO:66), Human collagen α3 KuDom (SE ID NO:68), Human TFPI-2 DOMAIN 1 (SEQ ID NO:70), Human TFPI-2 DOMAIN 2 (SEQ ID NO:72), Human TFPI-2 DOMAIN 3 (SEQ ID NO:74), HUMAN ITI-K1 (SEQ ID NO:76), Human ITI-K2 (SEQ ID NO:78), HUMAN PROTEASE NEXIN-II (SEQ ID NO:80), Human APP-I (SEQ ID NO:39), DPI-1.1.1 (SEQ ID NO:61), DPI-1.1.2 (SEQ ID NO:62), DPI-1.1.3 (SEQ ID NO:63), DPI-1.2.1 (SEQ ID NO:65), DPI-1.3.1 (SEQ ID NO:67), DPI-2.1 (SEQ ID NO:69), DPI-3.1.1 (SEQ ID NO:71), DPI 3.2.1 (SEQ ID NO:73), DPI-3.3.1 (SEQ ID NO:75), DPI-4.1.1 (SEQ ID NO:77), DPI-4.2.1 (SEQ ID NO:79), DPI-4.2.2 (SEQ ID NO: 130), DPI-4.2.3 (SEQ ID NO:131), DPI-4.2.4 (SEQ ID , DPI-4.2.5 (SEQ ID NO:133), DPI-5.1 (SEQ ID NO:81), DPI-5.2 (SEQ ID NO:82), DPI-6.1 (SEQ ID NO:125), and DPI-6.2 (SEQ ID NO:126).

4. A protein according to claim 3 comprising an amino-acid sequence that is selected from the group comprising SPI11 (SEQ ID NO:40), SPI15 (SEQ ID NO:41), SPI08 (SEQ ID NO:42), SPI23 (SEQ ID NO:43), SPI47 (SEQ ID NO:57), QS4 (SEQ ID NO:4), and NS4 (SEQ ID NO:11.

5. A protein according to claim 1 wherein the sequence is identical at residues 10–21 and 31–39 and has five or fewer differences at residues 5–9, 22–30, and 40–55 as compared to a reference sequence selected from the group comprising SPI11 (SEQ ID NO:40), SPI15 (SEQ ID NO:41), SPI08 (SEQ ID NO:42), SPI23 (SEQ ID NO:43), SPI47 (SEQ ID NO:57), QS4 (SEQ ID NO:4), and NS4(SEQ ID NO:11).

6. A protein according to claim 1, wherein Kunitz domain position 18 is Phe, position 15 is Arg, position 16 is Ala, and position 17 is Arg.

7. A protein according to claim 1, wherein said protein has a $K_i$ for human plasmin of 100 pM or less.

8. A protein according to claim 1, wherein Kunitz domain position 13 is Leu.

9. A protein according to claim 1, wherein Kunitz domain position 16 is Gly.

10. A protein according to claim 1, wherein Kunitz domain position 17 is Ser.

11. A protein according to claim 1 wherein Kunitz domain position 18 is Phe.

12. A protein according to claim 1, wherein Kunitz domain position 19 is Glu or Gln.

13. A protein according to claim 1, wherein Kunitz domain position 31 is Gln.

14. A protein according to claim 1, wherein Kunitz domain position 32 is Gln.

15. A protein according to claim 1, wherein the protein inhibits human plasmin with a $K_i$ of about 300 picomolar or less.

16. A plasmin inhibiting protein according to claim 1 having a $K_i$ of about 100 pM or less.

* * * * *

SEQUENCE LISTING (1) GENERAL INFORMATION:

(iii) NUMBER OF SEQUENCES: 137

(2) INFORMATION FOR SEQ ID NO:1:

(i) SEQUENCE CHARACTERISTICS:
        (A) LENGTH:304 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met Ile Tyr Thr Met Lys Lys Val His Ala Leu Trp Ala Ser Val Cys
 1               5                  10                  15

Leu Leu Leu Asn Leu Ala Pro Ala Pro Leu Asn Ala Asp Ser Glu Glu
                20                  25                  30

Asp Glu Glu His Thr Ile Ile Thr Asp Thr Glu Leu Pro Pro Leu Lys
            35                  40                  45

Leu Met His Ser Phe Cys Ala Phe Lys Ala Asp Asp Gly Pro Cys Lys
         50                  55                  60

Ala Ile Met Lys Arg Phe Phe Asn Ile Phe Thr Arg Gln Cys Glu
 65                  70                  75                  80

Glu Phe Ile Tyr Gly Gly Cys Glu Gly Asn Gln Asn Arg Phe Glu Ser
                 85                  90                  95

Leu Glu Glu Cys Lys Lys Met Cys Thr Arg Asp Asn Ala Asn Arg Ile
                100                 105                 110

Ile Lys Thr Thr Leu Gln Gln Glu Lys Pro Asp Phe Cys Phe Leu Glu
            115                 120                 125

```
Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
    290                 295                 300

(2) INFORMATION FOR SEQ ID NO:2:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met His Ser Phe Cys Ala Phe Lys Ala Asp Asp Gly Pro Cys Lys Ala
1               5                   10                  15

Ile Met Lys Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:3:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
                20                  25                  30

Phe Thr Tyr Gly Gly Cys Arg Gly Asn Gln Asn Arg Phe Glu Ser Leu
            35                  40                  45
```

```
Glu Glu Cys Lys Lys Met Cys Thr Arg Asp
    50                  55
```

(2) INFORMATION FOR SEQ ID NO:4:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Gln
                20                  25                  30

Phe Tyr Tyr Gly Gly Cys Asp Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:5:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Gln
                20                  25                  30

Phe His Tyr Gly Gly Cys Asp Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:6:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Gln
                20                  25                  30

Phe Asp Tyr Gly Gly Cys Ala Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:7:

(i) SEQUENCE CHARACTERISTICS:
    (A) LENGTH:58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:7:

```
Met His Ser Phe Cys Ala Phe Lys Ala Asp Asp Gly Pro Cys Lys Ala
 1               5                  10                  15
Arg Phe Glu Arg Phe Phe Phe Asn Ile Phe Thr Arg Gln Cys Gln Glu
                20                  25                  30
Phe Arg Tyr Gly Gly Cys Asp Gly Asn Gln Asn Arg Phe Glu Ser Leu
            35                  40                  45
Glu Glu Cys Lys Lys Met Cys Thr Arg Asp
    50                  55
```

(2) INFORMATION FOR SEQ ID NO:8:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met His Ser Phe Cys Ala Phe Lys Ala Asp Asp Gly Pro Cys Lys Ala
 1               5                  10                  15
Arg Phe Glu Arg Phe Phe Phe Asn Ile Phe Thr Arg Gln Cys Gln Gln
                20                  25                  30
Phe Tyr Tyr Gly Gly Cys Gln Gly Asn Gln Asn Arg Phe Glu Ser Leu
            35                  40                  45
Glu Glu Cys Lys Lys Met Cys Thr Arg Asp
    50                  55
```

(2) INFORMATION FOR SEQ ID NO:9:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met His Ser Phe Cys Ala Phe Lys Ala Asp Asp Gly Pro Cys Lys Ala
 1               5                  10                  15
Arg Phe Glu Arg Phe Phe Phe Asn Ile Phe Thr Arg Gln Cys Glu Glu
                20                  25                  30
Phe Ala Tyr Gly Gly Cys Gly Gly Asn Gln Asn Arg Phe Glu Ser Leu
            35                  40                  45
Glu Glu Cys Lys Lys Met Cys Thr Arg Asp
    50                  55
```

(2) INFORMATION FOR SEQ ID NO:10:

(i) SEQUENCE CHARACTERISTICS:
        (A) LENGTH:58 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:10:

Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Gln Gln
             20                  25                  30

Phe Val Tyr Gly Gly Cys Gly Gly Asn Gln Asn Arg Phe Glu Ser Leu
         35                  40                  45

Glu Glu Cys Lys Lys Met Cys Thr Arg Asp
 50                  55

(2) INFORMATION FOR SEQ ID NO:11:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Gln
             20                  25                  30

Phe Thr Tyr Gly Gly Cys Gly Gly Asn Gln Asn Arg Phe Glu Ser Leu
         35                  40                  45

Glu Glu Cys Lys Lys Met Cys Thr Arg Asp
 50                  55

(2) INFORMATION FOR SEQ ID NO:12:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Glu
             20                  25                  30

Phe Thr Tyr Gly Gly Cys Gly Gly Asn Gln Asn Arg Phe Glu Ser Leu
         35                  40                  45

Glu Glu Cys Lys Lys Met Cys Thr Arg Asp
 50                  55

(2) INFORMATION FOR SEQ ID NO:13:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Gln
            20                  25                  30

Phe Ile Tyr Gly Gly Cys Gln Gly Asn Gln Asn Arg Phe Glu Ser Leu
            35                  40                  45

Glu Glu Cys Lys Lys Met Cys Thr Arg Asp
50                      55

(2) INFORMATION FOR SEQ ID NO:14:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Gln
            20                  25                  30

Phe Ile Tyr Gly Gly Cys Gly Gly Asn Gln Asn Arg Phe Glu Ser Leu
            35                  40                  45

Glu Glu Cys Lys Lys Met Cys Thr Arg Asp
50                      55

(2) INFORMATION FOR SEQ ID NO:15:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Gln
            20                  25                  30

Phe Ile Tyr Gly Gly Cys Phe Gly Asn Gln Asn Arg Phe Glu Ser Leu
            35                  40                  45

Glu Glu Cys Lys Lys Met Cys Thr Arg Asp
50                      55

(2) INFORMATION FOR SEQ ID NO:16:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Gln Gln

```
                      20                  25                  30
Phe His Tyr Gly Gly Cys Glu Gly Asn Gln Asn Arg Phe Glu Ser Leu
         35                  40                  45

Glu Glu Cys Lys Lys Met Cys Thr Arg Asp
         50                  55
```

(2) INFORMATION FOR SEQ ID NO:17:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Met His Ser Phe Cys Ala Phe Lys Ala Asp Asp Gly Pro Cys Lys Ala
 1               5                  10                  15

Arg Phe Glu Arg Phe Phe Asn Ile Phe Thr Arg Gln Cys Glu Gln
                  20                  25                  30

Phe Val Tyr Gly Gly Cys Ala Gly Asn Gln Asn Arg Phe Glu Ser Leu
         35                  40                  45

Glu Glu Cys Lys Lys Met Cys Thr Arg Asp
         50                  55
```

(2) INFORMATION FOR SEQ ID NO:18:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Met His Ser Phe Cys Ala Phe Lys Ala Asp Asp Gly Pro Cys Lys Ala
 1               5                  10                  15

Arg Phe Glu Arg Phe Phe Asn Ile Phe Thr Arg Gln Cys Glu Gln
                  20                  25                  30

Phe Leu Tyr Gly Gly Cys Gly Gly Asn Gln Asn Arg Phe Glu Ser Leu
         35                  40                  45

Glu Glu Cys Lys Lys Met Cys Thr Arg Asp
         50                  55
```

(2) INFORMATION FOR SEQ ID NO:19:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Met His Ser Phe Cys Ala Phe Lys Ala Asp Asp Gly Pro Cys Lys Ala
 1               5                  10                  15

Arg Phe Glu Arg Phe Phe Asn Ile Phe Thr Arg Gln Cys Glu Gln
                  20                  25                  30

Phe Ile Tyr Gly Gly Cys Gly Gly Asn Gln Asn Arg Phe Glu Ser Leu
         35                  40                  45
```

```
Glu Glu Cys Lys Lys Met Cys Thr Arg Asp
    50                  55
```

(2) INFORMATION FOR SEQ ID NO:20:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Gln
            20                  25                  30

Phe Val Tyr Gly Gly Cys Gly Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:21:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Glu
            20                  25                  30

Phe Val Tyr Gly Gly Cys Gly Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:22:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Met His Ser Phe Cys Ala Phe Lys Ala Asp Asp Gly Leu Cys Lys Gly
1               5                   10                  15

Arg Phe Gln Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:23:

(i) SEQUENCE CHARACTERISTICS:
    (A) LENGTH:58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:23:

Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Gln
                20                  25                  30

Phe Thr Tyr Gly Gly Cys Met Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:24:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Gln
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:25:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

Met His Ser Phe Cys Ala Phe Lys Ala Asp Asp Gly Pro Cys Lys Ala
 1               5                  10                  15

Arg Phe Glu Arg Phe Phe Phe Asn Ile Phe Thr Arg Gln Cys Glu Glu
                20                  25                  30

Phe Leu Tyr Gly Gly Cys Leu Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:26:

(i) SEQUENCE CHARACTERISTICS:
        (A) LENGTH:58 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:26:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
            20                  25                  30

Phe Ser Tyr Gly Gly Cys Gln Gly Asn Gln Asn Arg Phe Glu Ser Leu
        35                  40                  45

Glu Glu Cys Lys Lys Met Cys Thr Arg Asp
50                  55

(2) INFORMATION FOR SEQ ID NO:27:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
            20                  25                  30

Phe Ala Tyr Gly Gly Cys Ala Gly Asn Gln Asn Arg Phe Glu Ser Leu
        35                  40                  45

Glu Glu Cys Lys Lys Met Cys Thr Arg Asp
50                  55

(2) INFORMATION FOR SEQ ID NO:28:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
            20                  25                  30

Phe Ile Tyr Gly Gly Cys Val Gly Asn Gln Asn Arg Phe Glu Ser Leu
        35                  40                  45

Glu Glu Cys Lys Lys Met Cys Thr Arg Asp
50                  55

(2) INFORMATION FOR SEQ ID NO:29:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Glu
            20                  25                  30

Phe Ser Tyr Gly Gly Cys Lys Gly Asn Gln Asn Arg Phe Glu Ser Leu
        35                  40                  45

Glu Glu Cys Lys Lys Met Cys Thr Arg Asp
50                      55

(2) INFORMATION FOR SEQ ID NO:30:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Met His Ser Phe Cys Ala Phe Lys Ala Asp Asp Gly Pro Cys Lys Ala
1               5                   10                  15

Arg Phe Glu Arg Phe Phe Asn Ile Phe Thr Arg Gln Cys Glu Glu
            20                  25                  30

Phe Val Tyr Gly Gly Cys Lys Gly Asn Gln Asn Arg Phe Glu Ser Leu
        35                  40                  45

Glu Glu Cys Lys Lys Met Cys Thr Arg Asp
50                      55

(2) INFORMATION FOR SEQ ID NO:31:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Met His Ser Phe Cys Ala Phe Lys Ala Asp Asp Gly Pro Cys Lys Ala
1               5                   10                  15

Ser Phe Glu Arg Phe Phe Asn Ile Phe Thr Arg Gln Cys Glu Gln
            20                  25                  30

Phe Thr Tyr Gly Gly Cys Asn Gly Asn Gln Asn Arg Phe Glu Ser Leu
        35                  40                  45

Glu Glu Cys Lys Lys Met Cys Thr Arg Asp
50                      55

(2) INFORMATION FOR SEQ ID NO:32:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Met His Ser Phe Cys Ala Phe Lys Ala Asp Asp Gly Pro Cys Lys Ala
1               5                   10                  15

Ser Phe Glu Arg Phe Phe Asn Ile Phe Thr Arg Gln Cys Glu Glu 20                  25                  30
Phe Thr Tyr Gly Gly Cys Leu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:33:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
                20                  25                  30

Phe Phe Tyr Gly Gly Cys His Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:34:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
                20                  25                  30

Phe Thr Tyr Gly Gly Cys Gly Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:35:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Met His Ser Phe Cys Ala Phe Lys Ala Asp Asp Gly Pro Cys Lys Ala
1               5                   10                  15

Arg Phe Glu Arg Phe Phe Phe Asn Ile Phe Thr Arg Gln Cys Glu Gln
                20                  25                  30

Phe Thr Tyr Gly Gly Cys Met Gly Asn Gln Asn Arg Phe Glu Ser Leu
            35                  40                  45

```
Glu Glu Cys Lys Lys Met Cys Thr Arg Asp
    50                  55
```

(2) INFORMATION FOR SEQ ID NO:36:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

```
Met His Ser Phe Cys Ala Phe Lys Ala Asp Asp Gly Pro Cys Lys Ala
  1               5                  10                  15

Arg Phe Glu Arg Phe Phe Asn Ile Phe Thr Arg Gln Cys Glu Gln
                20                  25                  30

Phe Thr Tyr Gly Gly Cys Gly Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:37:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Met His Ser Phe Cys Ala Phe Lys Ala Asp Asp Gly Pro Cys Lys Ala
  1               5                  10                  15

Arg Phe Glu Arg Phe Phe Asn Ile Phe Thr Arg Gln Cys Glu Gln
                20                  25                  30

Phe Val Tyr Gly Gly Cys Gly Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:38:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Arg Pro Asp Phe Cys Leu Glu Pro Pro Tyr Thr Gly Pro Cys Lys Ala
  1               5                  10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
    50                  55
```

(2) INFORMATION FOR SEQ ID NO:39:

(i) SEQUENCE CHARACTERISTICS:
    (A) LENGTH:58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:39:

Val Arg Glu Val Cys Ser Glu Gln Ala Glu Thr Gly Pro Cys Arg Ala
 1               5                  10                  15

Met Ile Ser Arg Trp Tyr Phe Asp Val Thr Glu Gly Lys Cys Ala Pro
             20                  25                  30

Phe Phe Tyr Gly Gly Cys Gly Gly Asn Arg Asn Asn Phe Asp Thr Glu
             35                  40                  45

Glu Tyr Cys Met Ala Val Cys Gly Ser Ala
 50                  55

(2) INFORMATION FOR SEQ ID NO:40:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

Met His Ser Phe Cys Ala Phe Lys Ala Glu Thr Gly Pro Cys Arg Ala
 1               5                  10                  15

Arg Phe Asp Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
 50                  55

(2) INFORMATION FOR SEQ ID NO:41:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Met His Ser Phe Cys Ala Phe Lys Ala Glu Ser Gly Pro Cys Arg Ala
 1               5                  10                  15

Arg Phe Asp Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
 50                  55

(2) INFORMATION FOR SEQ ID NO:42:

(i) SEQUENCE CHARACTERISTICS:
        (A) LENGTH:58 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:42:

Met His Ser Phe Cys Ala Phe Lys Ala Asp Gly Gly Pro Cys Arg Ala
 1               5                  10                  15

Arg Phe Glu Arg Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
 50                  55

(2) INFORMATION FOR SEQ ID NO:43:

(i) SEQUENCE CHARACTERISTICS:
          (A) LENGTH:58 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:43:

Met His Ser Phe Cys Ala Phe Lys Ala Glu Gly Gly Pro Cys Arg Ala
 1               5                  10                  15

Lys Phe Gln Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
 50                  55

(2) INFORMATION FOR SEQ ID NO:44:

(i) SEQUENCE CHARACTERISTICS:
          (A) LENGTH:58 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:44:

Met His Ser Phe Cys Ala Phe Lys Ala Asp Gly Gly Pro Cys Lys Gly
 1               5                  10                  15

Lys Phe Pro Arg Phe Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
 50                  55

(2) INFORMATION FOR SEQ ID NO:45:

(i) SEQUENCE CHARACTERISTICS:
          (A) LENGTH:58 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:45:

Met His Ser Phe Cys Ala Phe Lys Ala Glu Thr Gly Pro Cys Arg Ala
 1               5                  10                  15

Lys Phe Asp Arg Trp Phe Phe Asn Ile Phe Thr Arg Gln Cys Glu Ala
                20                  25                  30

Phe Val Tyr Gly Gly Cys Gly Gly Asn Gln Asn Arg Phe Glu Ser Leu
            35                  40                  45

Glu Glu Cys Lys Lys Met Cys Thr Arg Asp
50                  55

(2) INFORMATION FOR SEQ ID NO:46:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

Met His Ser Phe Cys Ala Phe Lys Ala Glu Thr Gly Pro Cys Arg Ala
 1               5                  10                  15

Lys Phe Asp Arg Trp Phe Phe Asn Ile Phe Thr Arg Gln Cys Glu Pro
                20                  25                  30

Phe Val Tyr Gly Gly Cys Glu Gly Asn Gln Asn Arg Phe Glu Ser Leu
            35                  40                  45

Glu Glu Cys Lys Lys Met Cys Thr Arg Asp
50                  55

(2) INFORMATION FOR SEQ ID NO:47:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Met His Ser Phe Cys Ala Phe Lys Ala Glu Thr Gly Pro Cys Arg Ala
 1               5                  10                  15

Lys Phe Asp Arg Trp Phe Phe Asn Ile Phe Thr Arg Gln Cys Asn Thr
                20                  25                  30

Phe Val Tyr Gly Gly Cys Gly Gly Asn Gln Asn Arg Phe Glu Ser Leu
            35                  40                  45

Glu Glu Cys Lys Lys Met Cys Thr Arg Asp
50                  55

(2) INFORMATION FOR SEQ ID NO:48:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Met His Ser Phe Cys Ala Phe Lys Ala Glu Thr Gly Pro Cys Arg Gly
 1               5                  10                  15

Lys Phe Asp Arg Trp Phe Phe Asn Ile Phe Thr Arg Gln Cys Gln Gly

```
                 20                  25                  30
Phe Val Tyr Gly Gly Cys Gly Asn Gln Asn Arg Phe Glu Ser Leu
             35                  40                  45
Glu Glu Cys Lys Lys Met Cys Thr Arg Asp
         50                  55
```

(2) INFORMATION FOR SEQ ID NO:49:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

```
Met His Ser Phe Cys Ala Phe Lys Ala Glu Val Gly Pro Cys Arg Ala
 1               5                  10                  15
Lys Phe Asp Arg Trp Phe Phe Asn Ile Phe Thr Arg Gln Cys His Leu
                 20                  25                  30
Phe Thr Tyr Gly Gly Cys Gly Asn Gln Asn Arg Phe Glu Ser Leu
             35                  40                  45
Glu Glu Cys Lys Lys Met Cys Thr Arg Asp
         50                  55
```

(2) INFORMATION FOR SEQ ID NO:50:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

```
Met His Ser Phe Cys Ala Phe Lys Ala Glu Thr Gly Pro Cys Arg Gly
 1               5                  10                  15
Lys Phe Asp Arg Trp Phe Phe Asn Ile Phe Thr Arg Gln Cys Ala Gln
                 20                  25                  30
Phe Val Tyr Gly Gly Cys Glu Asn Gln Asn Arg Phe Glu Ser Leu
             35                  40                  45
Glu Glu Cys Lys Lys Met Cys Thr Arg Asp
         50                  55
```

(2) INFORMATION FOR SEQ ID NO:51:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Met His Ser Phe Cys Ala Phe Lys Ala Glu Thr Gly Pro Cys Arg Gly
 1               5                  10                  15
Lys Phe Asp Arg Trp Phe Phe Asn Ile Phe Thr Arg Gln Cys Glu Ser
                 20                  25                  30
Phe His Tyr Gly Gly Cys Lys Gly Asn Gln Asn Arg Phe Glu Ser Leu
             35                  40                  45
```

```
Glu Glu Cys Lys Lys Met Cys Thr Arg Asp
    50                  55
```

(2) INFORMATION FOR SEQ ID NO:52:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

```
Met His Ser Phe Cys Ala Phe Lys Ala Asp Ala Gly Pro Cys Arg Ala
 1               5                  10                  15

Lys Phe Glu Arg Phe Phe Phe Asn Ile Phe Thr Arg Gln Cys Glu Ala
            20                  25                  30

Phe Leu Tyr Gly Gly Cys Gly Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:53:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Met His Ser Phe Cys Ala Phe Lys Ala Asp Val Gly Pro Cys Arg Ala
 1               5                  10                  15

Lys Phe Glu Arg Phe Phe Phe Asn Ile Phe Thr Arg Gln Cys Glu Ala
            20                  25                  30

Phe Leu Tyr Gly Gly Cys Glu Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:54:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
Met His Ser Phe Cys Ala Phe Lys Ala Asp Ala Gly Pro Cys Arg Ala
 1               5                  10                  15

Lys Phe Glu Arg Phe Phe Phe Asn Ile Phe Thr Arg Gln Cys Thr Ala
            20                  25                  30

Phe Phe Tyr Gly Gly Cys Gly Gly Asn Gln Asn Arg Phe Glu Ser Leu
            35                  40                  45

Glu Glu Cys Lys Lys Met Cys Thr Arg Asp
    50                  55
```

(2) INFORMATION FOR SEQ ID NO:55:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:55:

Met His Ser Phe Cys Ala Phe Lys Ala Asp Ser Gly Pro Cys Arg Ala
 1               5                  10                  15

Arg Phe Asp Arg Trp Phe Phe Asn Ile Phe Thr Arg Gln Cys Thr Arg
                20                  25                  30

Phe Pro Tyr Gly Gly Cys Gly Gly Asn Gln Asn Arg Phe Glu Ser Leu
                35                  40                  45

Glu Glu Cys Lys Lys Met Cys Thr Arg Asp
        50                  55

(2) INFORMATION FOR SEQ ID NO:56:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

Met His Ser Phe Cys Ala Phe Lys Ala Glu Thr Gly Pro Cys Arg Ala
 1               5                  10                  15

Lys Ile Pro Arg Leu Phe Phe Asn Ile Phe Thr Arg Gln Cys Glu Pro
                20                  25                  30

Phe Ile Trp Gly Gly Cys Gly Gly Asn Gln Asn Arg Phe Glu Ser Leu
                35                  40                  45

Glu Glu Cys Lys Lys Met Cys Thr Arg Asp
        50                  55

(2) INFORMATION FOR SEQ ID NO:57:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

Met His Ser Phe Cys Ala Phe Lys Ala Asp Ala Gly Pro Cys Arg Ala
 1               5                  10                  15

Lys Phe Glu Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
                35                  40                  45

Glu Glu Cys Lys Lys Met Cys Thr Arg Asp
        50                  55

(2) INFORMATION FOR SEQ ID NO:58:

(i) SEQUENCE CHARACTERISTICS:
        (A) LENGTH: 58 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:58:

Met His Ser Phe Cys Ala Phe Lys Ala Glu Thr Gly Pro Cys Lys Gly
 1               5                  10                  15

Ser Phe Asp Arg Trp Phe Phe Asn Ile Phe Thr Arg Gln Cys Asn Val
                20                  25                  30

Phe Arg Tyr Gly Gly Cys Arg Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:59:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Met His Ser Phe Cys Ala Phe Lys Ala Asp Ala Gly Pro Cys Arg Ala
 1               5                  10                  15

Arg Phe Glu Arg Phe Phe Phe Asn Ile Phe Thr Arg Gln Cys Asp Thr
                20                  25                  30

Phe Leu Tyr Gly Gly Cys Glu Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:60:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

Met His Ser Phe Cys Ala Phe Lys Ala Asp Ser Gly Pro Cys Lys Gly
 1               5                  10                  15

Arg Phe Gly Arg Leu Phe Phe Asn Ile Phe Thr Arg Gln Cys Thr Ala
                20                  25                  30

Phe Asp Trp Gly Gly Cys Gly Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:61:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

Met His Ser Phe Cys Ala Phe Lys Ala Asp Thr Gly Pro Cys Arg Ala
1               5                   10                  15

Arg Phe Asp Arg Phe Phe Asn Ile Phe Thr Arg Gln Cys Glu Ala
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
50                  55

(2) INFORMATION FOR SEQ ID NO:62:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

Met His Ser Phe Cys Ala Phe Lys Ala Asp Thr Gly Pro Cys Arg Ala
1               5                   10                  15

Arg Phe Asp Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
50                  55

(2) INFORMATION FOR SEQ ID NO:63:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

Met His Ser Phe Cys Ala Phe Lys Ala Asp Ala Gly Pro Cys Arg Ala
1               5                   10                  15

Arg Phe Asp Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
50                  55

(2) INFORMATION FOR SEQ ID NO:64:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg

```
                20                  25                  30
Phe Lys Tyr Gly Gly Cys Leu Gly Asn Met Asn Asn Phe Glu Thr Leu
         35                  40                  45

Glu Glu Cys Lys Asn Ile Cys Glu Asp Gly
         50                  55
```

(2) INFORMATION FOR SEQ ID NO:65:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

```
Lys Pro Asp Phe Cys Phe Leu Glu Glu Asp Thr Gly Pro Cys Arg Gly
 1               5                  10                  15

Arg Phe Asp Arg Tyr Phe Tyr Asn Asn Gln Thr Lys Gln Cys Glu Thr
                20                  25                  30

Phe Ile Tyr Gly Gly Cys Glu Gly Asn Met Asn Asn Phe Glu Thr Leu
         35                  40                  45

Glu Glu Cys Lys Asn Ile Cys Glu Asp Gly
         50                  55
```

(2) INFORMATION FOR SEQ ID NO:66:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:66:

```
Gly Pro Ser Trp Cys Leu Thr Pro Ala Asp Arg Gly Leu Cys Arg Ala
 1               5                  10                  15

Asn Glu Asn Arg Phe Tyr Tyr Asn Ser Val Ile Gly Lys Cys Arg Pro
                20                  25                  30

Phe Lys Tyr Ser Gly Cys Gly Asn Glu Asn Asn Phe Thr Ser Lys
         35                  40                  45

Gln Glu Cys Leu Arg Ala Cys Lys Lys Gly
         50                  55
```

(2) INFORMATION FOR SEQ ID NO:67:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:67:

```
Gly Pro Ser Trp Cys Leu Thr Pro Ala Asp Thr Gly Pro Cys Arg Ala
 1               5                  10                  15

Arg Phe Asp Arg Phe Tyr Tyr Asn Ser Val Ile Gly Lys Cys Glu Pro
                20                  25                  30

Phe Ile Tyr Gly Gly Cys Gly Gly Asn Glu Asn Asn Phe Thr Ser Lys
         35                  40                  45
```

```
Gln Glu Cys Leu Arg Ala Cys Lys Lys Gly
     50                  55
```

(2) INFORMATION FOR SEQ ID NO:68:

(i) SEQUENCE CHARACTERISTICS:
       (A) LENGTH:58 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:68:

```
Glu Thr Asp Ile Cys Lys Leu Pro Lys Asp Glu Gly Thr Cys Arg Asp
 1               5                  10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
        35                  40                  45

Lys Glu Cys Glu Lys Val Cys Ala Pro Val
     50                  55
```

(2) INFORMATION FOR SEQ ID NO:69:

(i) SEQUENCE CHARACTERISTICS:
       (A) LENGTH:58 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:69:

```
Glu Thr Asp Ile Cys Lys Leu Pro Lys Asp Thr Gly Pro Cys Arg Ala
 1               5                  10                  15

Arg Phe Asp Lys Trp Tyr Tyr Asp Pro Asn Thr Lys Ser Cys Glu Glu
            20                  25                  30

Phe Val Tyr Gly Gly Cys Gly Gly Asn Glu Asn Lys Phe Gly Ser Gln
        35                  40                  45

Lys Glu Cys Glu Lys Val Cys Ala Pro Val
     50                  55
```

(2) INFORMATION FOR SEQ ID NO:70:

(i) SEQUENCE CHARACTERISTICS:
       (A) LENGTH:58 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:70:

```
Asn Ala Glu Ile Cys Leu Leu Pro Leu Asp Tyr Gly Pro Cys Arg Ala
 1               5                  10                  15

Leu Leu Leu Arg Tyr Tyr Tyr Asp Arg Tyr Thr Gln Ser Cys Arg Gln
            20                  25                  30

Phe Leu Tyr Gly Gly Cys Glu Gly Asn Ala Asn Asn Phe Tyr Thr Trp
        35                  40                  45

Glu Ala Cys Asp Asp Ala Cys Trp Arg Ile
     50                  55
```

(2) INFORMATION FOR SEQ ID NO:71:

(i) SEQUENCE CHARACTERISTICS:
    (A) LENGTH:58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:71:

Asn Ala Glu Ile Cys Leu Leu Pro Leu Asp Thr Gly Pro Cys Arg Ala
 1               5                  10                  15

Arg Phe Asp Arg Tyr Tyr Tyr Asp Arg Tyr Thr Gln Ser Cys Glu Gln
                20                  25                  30

Phe Leu Tyr Gly Gly Cys Glu Gly Asn Ala Asn Asn Phe Tyr Thr Trp
            35                  40                  45

Glu Ala Cys Asp Asp Ala Cys Trp Arg Ile
        50                  55

(2) INFORMATION FOR SEQ ID NO:72:

(i) SEQUENCE CHARACTERISTICS:
        (A) LENGTH:61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:72:

Val Pro Lys Val Cys Arg Leu Gln Val Ser Val Asp Asp Gln Cys Glu
 1               5                  10                  15

Gly Ser Thr Glu Lys Tyr Phe Phe Asn Leu Ser Ser Met Thr Cys Glu
                20                  25                  30

Lys Phe Phe Ser Gly Gly Cys His Arg Asn Arg Ile Glu Asn Arg Phe
            35                  40                  45

Pro Asp Glu Ala Thr Cys Met Gly Phe Cys Ala Pro Lys
        50                  55                  60

(2) INFORMATION FOR SEQ ID NO:73:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:73:

Val Pro Lys Val Cys Arg Leu Gln Val Glu Thr Gly Pro Cys Arg Gly
 1               5                  10                  15

Lys Phe Glu Lys Tyr Phe Phe Asn Leu Ser Ser Met Thr Cys Glu Thr
                20                  25                  30

Phe Val Tyr Gly Gly Cys Glu Gly Asn Arg Asn Arg Phe Pro Asp Glu
            35                  40                  45

Ala Thr Cys Met Gly Phe Cys Ala Pro Lys
        50                  55

(2) INFORMATION FOR SEQ ID NO:74:

(i) SEQUENCE CHARACTERISTICS:
        (A) LENGTH:58 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:74:

Ile Pro Ser Phe Cys Tyr Ser Pro Lys Asp Glu Gly Leu Cys Ser Ala
 1               5                  10                  15

Asn Val Thr Arg Tyr Tyr Phe Asn Pro Arg Tyr Arg Thr Cys Asp Ala
                20                  25                  30

Phe Thr Tyr Thr Gly Cys Gly Gly Asn Asp Asn Asn Phe Val Ser Arg
            35                  40                  45

Glu Asp Cys Lys Arg Ala Cys Ala Lys Ala
        50                  55

(2) INFORMATION FOR SEQ ID NO:75:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:75:

Ile Pro Ser Phe Cys Tyr Ser Pro Lys Asp Thr Gly Pro Cys Arg Ala
 1               5                  10                  15

Arg Phe Thr Arg Tyr Tyr Phe Asn Pro Arg Tyr Arg Thr Cys Asp Ala
                20                  25                  30

Phe Thr Tyr Gly Gly Cys Gly Gly Asn Asp Asn Asn Phe Val Ser Arg
            35                  40                  45

Glu Asp Cys Lys Arg Ala Cys Ala Lys Ala
        50                  55

(2) INFORMATION FOR SEQ ID NO:76:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Lys Glu Asp Ser Cys Gln Leu Gly Tyr Ser Ala Gly Pro Cys Met Gly
 1               5                  10                  15

Met Thr Ser Arg Tyr Phe Tyr Asn Gly Thr Ser Met Ala Cys Glu Thr
                20                  25                  30

Phe Gln Tyr Gly Gly Cys Met Gly Asn Gly Asn Asn Phe Val Thr Glu
            35                  40                  45

Lys Glu Cys Leu Gln Thr Cys Arg Thr Val
        50                  55

(2) INFORMATION FOR SEQ ID NO:77:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:77:

```
Lys Glu Asp Ser Cys Gln Leu Gly Tyr Glu Ala Gly Pro Cys Arg Gly
 1               5                  10                  15

Lys Phe Ser Arg Tyr Phe Tyr Asn Gly Thr Ser Met Ala Cys Glu Thr
                 20                  25                  30

Phe Val Tyr Gly Gly Cys Gly Gly Asn Gly Asn Asn Phe Val Thr Glu
             35                  40                  45

Lys Glu Cys Leu Gln Thr Cys Arg Thr Val
 50                  55
```

(2) INFORMATION FOR SEQ ID NO:78:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:78:

```
Thr Val Ala Ala Cys Asn Leu Pro Ile Val Arg Gly Pro Cys Arg Ala
 1               5                  10                  15

Phe Ile Gln Leu Trp Ala Phe Asp Ala Val Lys Gly Lys Cys Val Leu
                 20                  25                  30

Phe Pro Tyr Gly Gly Cys Gln Gly Asn Gly Asn Lys Phe Tyr Ser Glu
             35                  40                  45

Lys Glu Cys Arg Glu Tyr Cys Gly Val Pro
 50                  55
```

(2) INFORMATION FOR SEQ ID NO:79:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:79:

```
Thr Val Ala Ala Cys Asn Leu Pro Ile Asp Thr Gly Pro Cys Arg Ala
 1               5                  10                  15

Arg Phe Gln Leu Trp Ala Phe Asp Ala Val Lys Gly Lys Cys Val Leu
                 20                  25                  30

Phe Val Tyr Gly Gly Cys Gln Gly Asn Gly Asn Lys Phe Tyr Ser Glu
             35                  40                  45

Lys Glu Cys Arg Glu Tyr Cys Gly Val Pro
 50                  55
```

(2) INFORMATION FOR SEQ ID NO:80:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:80:

```
Val Arg Glu Val Cys Ser Glu Gln Ala Glu Thr Gly Pro Cys Arg Ala
 1               5                  10                  15

Met Ile Ser Arg Trp Tyr Phe Asp Val Thr Glu Gly Lys Cys Ala Pro
```

```
             20                  25                  30
Phe Phe Tyr Gly Gly Cys Gly Gly Asn Arg Asn Asn Phe Asp Thr Glu
         35                  40                  45

Glu Tyr Cys Met Ala Val Cys Gly Ser Ala
         50                  55
```

(2) INFORMATION FOR SEQ ID NO:81:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:81:

```
Val Arg Glu Val Cys Ser Glu Gln Ala Glu Thr Gly Pro Cys Arg Ala
 1               5                  10                  15

Arg Phe Ser Arg Trp Tyr Phe Asp Val Thr Glu Gly Lys Cys Ala Pro
             20                  25                  30

Phe Phe Tyr Gly Gly Cys Gly Gly Asn Arg Asn Asn Phe Asp Thr Glu
         35                  40                  45

Glu Tyr Cys Met Ala Val Cys Gly Ser Ala
         50                  55
```

(2) INFORMATION FOR SEQ ID NO:82:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:82:

```
Val Arg Glu Val Cys Ser Glu Gln Ala Glu Thr Gly Pro Cys Arg Ala
 1               5                  10                  15

Arg Phe Ser Arg Trp Tyr Phe Asp Val Thr Glu Gly Lys Cys Glu Pro
             20                  25                  30

Phe Ile Tyr Gly Gly Cys Gly Gly Asn Arg Asn Asn Phe Asp Thr Glu
         35                  40                  45

Glu Tyr Cys Met Ala Val Cys Gly Ser Ala
         50                  55
```

(2) INFORMATION FOR SEQ ID NO:83:

(i) SEQUENCE CHARACTERISTICS:
        (A) LENGTH:97 bases
        (B) TYPE: nucleic acid
        (C) STRANDEDNESS: single
        (D) TOPOLOGY: linear (ii) MOLECULE TYPE:other nucleic acid
        (A) DESCRIPTION:synthetic DNA fragment (xi) SEQUENCE DESCRIPTION: SEQ ID NO:83:

```
CCTCCTATGC ATTCCTTCTG CGCCTTCAAG GCTRASRNTG GTNCTTGTAR        50

AGSTANSWTC NNSCGTTKST TCTTCAACAT CTTCACGCGT TCCCTCC           97
```

(2) INFORMATION FOR SEQ ID NO:84:

(i) SEQUENCE CHARACTERISTICS:

(A) LENGTH:26 bases
            (B) TYPE: nucleic acid
            (C) STRANDEDNESS: single
            (D) TOPOLOGY: linear (ii) MOLECULE TYPE:other nucleic acid
            (A) DESCRIPTION:synthetic DNA fragment (xi) SEQUENCE DESCRIPTION: SEQ ID NO:84:

GGAGGGAACG CGTGAAGATG TTGAAG                                    26

(2) INFORMATION FOR SEQ ID NO:85:

(i) SEQUENCE CHARACTERISTICS:
            (A) LENGTH:28 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:85:

Met His Ser Phe Cys Ala Phe Lys Ala Xaa Xaa Gly Xaa Cys Xaa Xaa
 1               5                  10                  15

Xaa Xaa Xaa Arg Xaa Phe Phe Asn Ile Phe Thr Arg
            20                  25

(2) INFORMATION FOR SEQ ID NO:86:

(i) SEQUENCE CHARACTERISTICS:
            (A) LENGTH:77 bases
            (B) TYPE: nucleic acid
            (C) STRANDEDNESS: single
            (D) TOPOLOGY: linear (ii) MOLECULE TYPE:other nucleic acid
            (A) DESCRIPTION:synthetic DNA fragment (xi) SEQUENCE DESCRIPTION: SEQ ID NO:86:

CCTCCTACGC GTCAGTGCNN SNNSTTCNNT TRSGGTGGTT GTRRGGGTAA           50

CCAGGTCGTG CTCTTTAGCA CGACCTG                                   77

(2) INFORMATION FOR SEQ ID NO:87:

(i) SEQUENCE CHARACTERISTICS:
            (A) LENGTH:16 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:87:

Thr Arg Gln Cys Xaa Xaa Phe Xaa Xaa Gly Gly Cys Xaa Gly Asn Gln
 1               5                  10                  15

(2) INFORMATION FOR SEQ ID NO:88:

(i) SEQUENCE CHARACTERISTICS:
            (A) LENGTH:58 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:88:

Met His Ser Phe Cys Ala Phe Lys Ala Glu Thr Gly Pro Cys Arg Ala
 1               5                  10                  15

```
Arg Phe Glu Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
            50                  55

(2) INFORMATION FOR SEQ ID NO:89:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:89:

Met His Ser Phe Cys Ala Phe Lys Ala Glu Thr Gly Pro Cys Arg Ala
 1               5                  10                  15

Arg Phe Gly Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
            50                  55

(2) INFORMATION FOR SEQ ID NO:90:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:90:

Met His Ser Phe Cys Ala Phe Lys Ala Glu Ser Gly Pro Cys Arg Ala
 1               5                  10                  15

Arg Phe Asp Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
            50                  55

(2) INFORMATION FOR SEQ ID NO:91:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:91:

Met His Ser Phe Cys Ala Phe Lys Ala Asp Thr Gly Pro Cys Arg Gly
 1               5                  10                  15

Arg Phe Glu Arg Leu Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
```

```
              35                  40                  45
Glu Glu Cys Lys Lys Met Cys Thr Arg Asp
 50                  55
```

(2) INFORMATION FOR SEQ ID NO:92:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:92:

```
Met His Ser Phe Cys Ala Phe Lys Ala Glu Thr Gly Ser Cys Arg Gly
  1               5                  10                  15

Arg Phe Asp Arg Trp Phe Phe Asn Ile Phe Thr Arg Gln Cys Glu Glu
                 20                  25                  30

Phe Ile Tyr Gly Gly Cys Glu Gly Asn Gln Asn Arg Phe Glu Ser Leu
              35                  40                  45

Glu Glu Cys Lys Lys Met Cys Thr Arg Asp
 50                  55
```

(2) INFORMATION FOR SEQ ID NO:93:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:93:

```
Met His Ser Phe Cys Ala Phe Lys Ala Glu Val Gly Pro Cys Arg Ala
  1               5                  10                  15

Ser Phe Pro Arg Trp Phe Phe Asn Ile Phe Thr Arg Gln Cys Glu Glu
                 20                  25                  30

Phe Ile Tyr Gly Gly Cys Glu Gly Asn Gln Asn Arg Phe Glu Ser Leu
              35                  40                  45

Glu Glu Cys Lys Lys Met Cys Thr Arg Asp
 50                  55
```

(2) INFORMATION FOR SEQ ID NO:94:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:94:

```
Met His Ser Phe Cys Ala Phe Lys Ala Glu Thr Gly Pro Cys Arg Ala
  1               5                  10                  15

Thr Phe Pro Arg Phe Phe Asn Ile Phe Thr Arg Gln Cys Glu Glu
                 20                  25                  30

Phe Ile Tyr Gly Gly Cys Glu Gly Asn Gln Asn Arg Phe Glu Ser Leu
              35                  40                  45

Glu Glu Cys Lys Lys Met Cys Thr Arg Asp
 50                  55
```

(2) INFORMATION FOR SEQ ID NO:95:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:95:

Met His Ser Phe Cys Ala Phe Lys Ala Glu Val Gly Pro Cys Arg Ala
 1               5                  10                  15

Ser Phe His Arg Trp Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:96:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:96:

Met His Ser Phe Cys Ala Phe Lys Ala Asp Thr Gly Pro Cys Arg Ala
 1               5                  10                  15

Ser Phe Gly Arg Trp Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:97:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:97:

Met His Ser Phe Cys Ala Phe Lys Ala Glu Thr Gly Pro Cys Arg Gly
 1               5                  10                  15

Met Phe Pro Arg Trp Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:98:

(i) SEQUENCE CHARACTERISTICS:
        (A) LENGTH:58 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:98:

Met His Ser Phe Cys Ala Phe Lys Ala Glu Gly Gly Pro Cys Arg Ala
 1               5                  10                  15

Arg Phe Asn Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:99:

(i) SEQUENCE CHARACTERISTICS:
            (A) LENGTH:58 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:99:

Met His Ser Phe Cys Ala Phe Lys Ala Glu Thr Gly Pro Cys Arg Ala
 1               5                  10                  15

Arg Ile Ser Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:100:

(i) SEQUENCE CHARACTERISTICS:
            (A) LENGTH:58 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:100:

Met His Ser Phe Cys Ala Phe Lys Ala Glu Gly Gly Pro Cys Arg Ala
 1               5                  10                  15

Lys Phe Glu Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55

(2) INFORMATION FOR SEQ ID NO:101:

(i) SEQUENCE CHARACTERISTICS:
            (A) LENGTH:58 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:101:

Met His Ser Phe Cys Ala Phe Lys Ala Asp Ser Gly Ala Cys Arg Gly
1               5                   10                  15

Arg Phe Glu Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:102:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:102:

Met His Ser Phe Cys Ala Phe Lys Ala Asp Ser Gly Pro Cys Arg Gly
1               5                   10                  15

Arg Phe Glu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:103:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:103:

Met His Ser Phe Cys Ala Phe Lys Ala Asp Thr Gly Pro Cys Arg Ala
1               5                   10                  15

Ser Phe Pro Arg Leu Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:104:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:104:

Met His Ser Phe Cys Ala Phe Lys Ala Glu Val Gly Pro Cys Arg Ala
1               5                   10                  15

Arg Ile Gln Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

(2) INFORMATION FOR SEQ ID NO:105:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:105:

Met His Ser Phe Cys Ala Phe Lys Ala Glu Ser Gly Pro Cys Arg Ala
 1               5                  10                  15

Lys Phe Ala Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

(2) INFORMATION FOR SEQ ID NO:106:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:106:

Met His Ser Phe Cys Ala Phe Lys Ala Glu Gly Gly Pro Cys Arg Ala
 1               5                  10                  15

Lys Phe Ala Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

(2) INFORMATION FOR SEQ ID NO:107:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:107:

Met His Ser Phe Cys Ala Phe Lys Ala Asp Thr Gly Ser Cys Arg Ala
 1               5                  10                  15

Lys Ile Glu Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu

```
                35                  40                  45
Glu Glu Cys Lys Lys Met Cys Thr Arg Asp
 50                  55
```

(2) INFORMATION FOR SEQ ID NO:108:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:108:

```
Met His Ser Phe Cys Ala Phe Lys Ala Asp Ser Gly Pro Cys Lys Ala
 1               5                  10                  15
Arg Phe Asp Arg Trp Phe Phe Asn Ile Phe Thr Arg Gln Cys Glu Glu
                20                  25                  30
Phe Ile Tyr Gly Gly Cys Glu Gly Asn Gln Asn Arg Phe Glu Ser Leu
                35                  40                  45
Glu Glu Cys Lys Lys Met Cys Thr Arg Asp
 50                  55
```

(2) INFORMATION FOR SEQ ID NO:109:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:109:

```
Met His Ser Phe Cys Ala Phe Lys Ala Asp Gly Gly Pro Cys Lys Gly
 1               5                  10                  15
Arg Phe Glu Arg Trp Phe Phe Asn Ile Phe Thr Arg Gln Cys Glu Glu
                20                  25                  30
Phe Ile Tyr Gly Gly Cys Glu Gly Asn Gln Asn Arg Phe Glu Ser Leu
                35                  40                  45
Glu Glu Cys Lys Lys Met Cys Thr Arg Asp
 50                  55
```

(2) INFORMATION FOR SEQ ID NO:110:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:110:

```
Met His Ser Phe Cys Ala Phe Lys Ala Glu Val Gly Ala Cys Lys Gly
 1               5                  10                  15
Arg Phe His Arg Trp Phe Phe Asn Ile Phe Thr Arg Gln Cys Glu Glu
                20                  25                  30
Phe Ile Tyr Gly Gly Cys Glu Gly Asn Gln Asn Arg Phe Glu Ser Leu
                35                  40                  45
Glu Glu Cys Lys Lys Met Cys Thr Arg Asp
 50                  55
```

(2) INFORMATION FOR SEQ ID NO:111:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:111:

```
Met His Ser Phe Cys Ala Phe Lys Ala Asp Gly Gly Pro Cys Arg Ala
 1               5                  10                  15

Ser Phe Pro Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55
```

(2) INFORMATION FOR SEQ ID NO:112:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:112:

```
Met His Ser Phe Cys Ala Phe Lys Ala Asp Ser Gly Ala Cys Arg Ala
 1               5                  10                  15

Met Phe His Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55
```

(2) INFORMATION FOR SEQ ID NO:113:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:113:

```
Met His Ser Phe Cys Ala Phe Lys Ala Asp Ser Gly Ala Cys Arg Ala
 1               5                  10                  15

Lys Phe Arg Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55
```

(2) INFORMATION FOR SEQ ID NO:114:

(i) SEQUENCE CHARACTERISTICS:
        (A) LENGTH:58 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:114:

Met His Ser Phe Cys Ala Phe Lys Ala Asp Ser Gly Thr Cys Lys Ala
1               5                   10                  15

Arg Phe Pro Arg Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:115:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:115:

Met His Ser Phe Cys Ala Phe Lys Ala Glu Thr Gly Pro Cys Lys Gly
1               5                   10                  15

Lys Ile Ala Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:116:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:116:

Met His Ser Phe Cys Ala Phe Lys Ala Asp Ser Gly Ala Cys Lys Gly
1               5                   10                  15

Lys Phe Glu Arg Trp Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

(2) INFORMATION FOR SEQ ID NO:117:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:117:

Met His Ser Phe Cys Ala Phe Lys Ala Glu Thr Gly Pro Cys Ala Ala
 1               5                  10                  15

Arg Phe Asp Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
         50                  55

(2) INFORMATION FOR SEQ ID NO:118:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:118:

Met His Ser Phe Cys Ala Phe Lys Ala Glu Thr Gly Pro Cys Gly Ala
 1               5                  10                  15

Arg Phe Asp Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
         50                  55

(2) INFORMATION FOR SEQ ID NO:119:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:119:

Met His Ser Phe Cys Ala Phe Lys Ala Glu Thr Gly Pro Cys Asn Ala
 1               5                  10                  15

Arg Phe Asp Arg Trp Phe Phe Asn Ile Phe Thr Arg Gln Cys Glu Ala
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
         50                  55

(2) INFORMATION FOR SEQ ID NO:120:

(i) SEQUENCE CHARACTERISTICS:
        (A) LENGTH:96 bases
        (B) TYPE: nucleic acid
        (C) STRANDEDNESS: single
        (D) TOPOLOGY: linear (ii) MOLECULE TYPE:other nucleic acid
        (A) DESCRIPTION:synthetic DNA fragment (xi) SEQUENCE DESCRIPTION: SEQ ID NO:120:

CCTCCTATGC ATTCCTTCTG CGCCTTCAAG GCTGASNCTN NTNNTNNTAR    50

```
ARNTARATTC GNSCRTTKST TCTTCAACAT CTTCACGCGT CAGTGC          96
```

(2) INFORMATION FOR SEQ ID NO:121:

(i) SEQUENCE CHARACTERISTICS:
        (A) LENGTH:71 bases
        (B) TYPE: nucleic acid
        (C) STRANDEDNESS: single
        (D) TOPOLOGY: linear (ii) MOLECULE TYPE:other nucleic acid
        (A) DESCRIPTION:synthetic DNA fragment (xi) SEQUENCE DESCRIPTION: SEQ ID NO:121:

```
CCTCCTCCCT GGTTACCSNY ANNANNACCG TAAACGAAAG CCTCGCACTG     50

ACGCGTGAAG ATGTTGAAGA A                                   71
```

(2) INFORMATION FOR SEQ ID NO:122:

(i) SEQUENCE CHARACTERISTICS:
        (A) LENGTH:42 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:122:

```
Met His Ser Phe Cys Ala Phe Lys Ala Xaa Xaa Xaa Xaa Xaa Xaa Xaa
 1               5                  10                  15

Xaa Phe Xaa Xaa Xaa Phe Phe Asn Ile Phe Thr Arg Gln Cys Glu Ala
            20                  25                  30

Phe Val Tyr Gly Xaa Xaa Xaa Gly Asn Gln
            35                  40
```

(2) INFORMATION FOR SEQ ID NO:123:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:123:

```
Xaa Xaa Xaa Xaa Cys Xaa Xaa Xaa Xaa Xaa Gly Xaa Cys Xaa Xaa
 1               5                  10                  15

Xaa Xaa Xaa Xaa Xaa Xaa Xaa Xaa Xaa Xaa Xaa Xaa Cys Xaa Xaa
            20                  25                  30

Phe Xaa Xaa Xaa Gly Cys Xaa Xaa Xaa Xaa Xaa Xaa Xaa Xaa Xaa
            35                  40                  45

Xaa Xaa Cys Xaa Xaa Xaa Cys Xaa Xaa Xaa
            50                  55
```

(2) INFORMATION FOR SEQ ID NO:124:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:124:

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
        35                  40                  45

Glu Lys Cys Glu Lys Phe Cys Lys Phe Thr
50                  55

(2) INFORMATION FOR SEQ ID NO:125:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:125:

Leu Pro Asn Val Cys Ala Phe Pro Met Glu Thr Gly Pro Cys Arg Ala
1               5                   10                  15

Arg Phe Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
        35                  40                  45

Glu Lys Cys Glu Lys Phe Cys Lys Phe Thr
50                  55

(2) INFORMATION FOR SEQ ID NO:126:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:126:

Leu Pro Asn Val Cys Ala Phe Pro Met Glu Thr Gly Pro Cys Arg Ala
1               5                   10                  15

Arg Phe Asp Arg Trp Phe Phe Asn Phe Glu Thr Gly Glu Cys Glu Leu
            20                  25                  30

Phe Val Tyr Gly Gly Cys Gly Gly Asn Ser Asn Asn Phe Leu Arg Lys
        35                  40                  45

Glu Lys Cys Glu Lys Phe Cys Lys Phe Thr
50                  55

(2) INFORMATION FOR SEQ ID NO:127:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:127:

Met His Ser Phe Cys Ala Phe Lys Ala Asp Thr Gly Pro Cys Lys Ala
1               5                   10                  15

Arg Phe Asp Arg Phe Phe Phe Asn Ile Phe Thr Arg Gln Cys Glu Ala

```
                        20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:128:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:128:

Met His Ser Phe Cys Ala Phe Lys Ala Asp Asp Gly Pro Cys Lys Ala
 1               5                  10                  15

Arg Phe Asp Arg Phe Phe Phe Asn Ile Phe Thr Arg Gln Cys Glu Glu
                    20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:129:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:129:

Met His Ser Phe Cys Ala Phe Lys Ala Asp Asp Gly Pro Cys Lys Ala
 1               5                  10                  15

Arg Phe Lys Arg Phe Phe Phe Asn Ile Phe Thr Arg Gln Cys Glu Glu
                    20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

(2) INFORMATION FOR SEQ ID NO:130:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:130:

Thr Val Ala Ala Cys Asn Leu Pro Ile Val Thr Gly Pro Cys Arg Ala
 1               5                  10                  15

Arg Phe Gln Leu Trp Ala Phe Asp Ala Val Lys Gly Lys Cys Val Leu
                    20                  25                  30

Phe Pro Tyr Gly Gly Cys Gln Gly Asn Gly Asn Lys Phe Tyr Ser Glu
            35                  40                  45
```

```
Lys Glu Cys Arg Glu Tyr Cys Gly Val Pro
    50                  55
```

(2) INFORMATION FOR SEQ ID NO:131:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:131:

```
Thr Val Ala Ala Cys Asn Leu Pro Ile Val Thr Gly Pro Cys Arg Ala
1               5                   10                  15
Arg Phe Gln Arg Trp Ala Phe Asp Ala Val Lys Gly Lys Cys Val Leu
                20                  25                  30
Phe Pro Tyr Gly Gly Cys Gln Gly Asn Gly Asn Lys Phe Tyr Ser Glu
            35                  40                  45
Lys Glu Cys Arg Glu Tyr Cys Gly Val Pro
    50                  55
```

(2) INFORMATION FOR SEQ ID NO:132:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:132:

```
Thr Val Ala Ala Cys Asn Leu Pro Ile Val Thr Gly Pro Cys Arg Ala
1               5                   10                  15
Arg Phe Gln Arg Trp Ala Phe Asp Ala Val Lys Gly Lys Cys Val Leu
                20                  25                  30
Phe Val Tyr Gly Gly Cys Gln Gly Asn Gly Asn Lys Phe Tyr Ser Glu
            35                  40                  45
Lys Glu Cys Arg Glu Tyr Cys Gly Val Pro
    50                  55
```

(2) INFORMATION FOR SEQ ID NO:133:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:133:

```
Thr Val Ala Ala Cys Asn Leu Pro Ile Glu Thr Gly Pro Cys Arg Ala
1               5                   10                  15
Arg Phe Asp Arg Trp Ala Phe Asp Ala Val Lys Gly Lys Cys Glu Thr
                20                  25                  30
Phe Val Tyr Gly Gly Cys Gly Gly Asn Gly Asn Lys Phe Tyr Ser Glu
            35                  40                  45
Lys Glu Cys Arg Glu Tyr Cys Gly Val Pro
    50                  55
```

(2) INFORMATION FOR SEQ ID NO:134:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:134:

Arg Pro Asp Phe Cys Leu Glu Pro Pro Tyr Thr Gly Pro Cys Lys Ala
 1               5                  10                  15

Arg Phe Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

(2) INFORMATION FOR SEQ ID NO:135:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:135:

Arg Pro Asp Phe Cys Leu Glu Pro Pro Tyr Thr Gly Pro Cys Arg Ala
 1               5                  10                  15

Arg Phe Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

(2) INFORMATION FOR SEQ ID NO:136:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:136:

Arg Pro Asp Phe Cys Leu Glu Pro Pro Tyr Thr Gly Pro Cys Arg Ala
 1               5                  10                  15

Arg Phe Ile Arg Tyr Phe Tyr Asn Ala Lys Ala Gly Leu Cys Gln Thr
            20                  25                  30

Phe Val Tyr Gly Gly Cys Gly Ala Lys Arg Asn Asn Phe Lys Ser Ala
        35                  40                  45

Glu Asp Cys Met Arg Thr Cys Gly Gly Ala
    50                  55

(2) INFORMATION FOR SEQ ID NO:137:

(i) SEQUENCE CHARACTERISTICS:
        (A) LENGTH: 58 amino acids
        (B) TYPE: amino acid
        (C) STRANDEDNESS: single -continued

```
        (D) TOPOLOGY: linear (ii) MOLECULE TYPE: protein (xi) SEQUENCE DESCRIPTION: SEQ ID NO:137:

Arg Pro Asp Phe Cys Leu Glu Pro Pro Asp Thr Gly Pro Cys Arg Ala
 1               5                  10                  15

Arg Phe Asp Arg Tyr Phe Tyr Asn Ala Lys Ala Gly Leu Cys Glu Thr
            20                  25                  30

Phe Val Tyr Gly Gly Cys Gly Ala Lys Arg Asn Asn Phe Lys Ser Ala
        35                  40                  45

Glu Asp Cys Met Arg Thr Cys Gly Gly Ala
     50                  55
```